(12) United States Patent
Edmonson et al.

(10) Patent No.: US 10,143,847 B1
(45) Date of Patent: Dec. 4, 2018

(54) DETERMINING A POSITION FOR AN IMPLANTABLE MEDICAL DEVICE

(71) Applicant: Medtronic, Inc., Minneapolis, MN (US)

(72) Inventors: Jonathan D. Edmonson, Blaine, MN (US); Matthew J. Hoffman, St. Paul, MN (US); Wei Jiang, Columbia, SC (US); Yanzhu Zhao, Blaine, MN (US); Srikara V. Peelukhana, Maple Grove, MN (US); Wei Gan, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/655,043

(22) Filed: Jul. 20, 2017

(51) Int. Cl.
| | |
|---|---|
| *A61N 1/37* | (2006.01) |
| *A61N 1/372* | (2006.01) |
| *A61N 1/378* | (2006.01) |
| *A61N 1/36* | (2006.01) |
| *A61N 1/04* | (2006.01) |
| *A61N 1/05* | (2006.01) |

(52) U.S. Cl.
CPC ..... *A61N 1/37252* (2013.01); *A61N 1/36135* (2013.01); *A61N 1/3787* (2013.01); *A61N 1/0476* (2013.01); *A61N 1/05* (2013.01)

(58) Field of Classification Search
None
See application file for complete search history.

(56) References Cited

U.S. PATENT DOCUMENTS

| | | |
|---|---|---|
| 4,603,705 A | 8/1986 | Speicher et al. |
| 4,987,897 A | 1/1991 | Funke |
| 5,113,859 A | 5/1992 | Funke |
| 5,117,824 A | 6/1992 | Keimel et al. |
| 5,697,377 A | 12/1997 | Wittkampf |
| 5,983,126 A | 11/1999 | Wittkampf |
| 6,009,878 A | 1/2000 | Weijand et al. |
| 6,112,116 A | 8/2000 | Fischell et al. |
| 6,496,715 B1 | 12/2002 | Lee et al. |

(Continued)

FOREIGN PATENT DOCUMENTS

| | | |
|---|---|---|
| WO | 2000059376 A1 | 10/2000 |
| WO | 2006012630 A2 | 2/2006 |
| WO | 2009056167 A1 | 5/2009 |

*Primary Examiner* — Ankit D Tejani

(57) ABSTRACT

In some examples, this disclosure describes a method for identifying a position within a patient for a first implantable medical device (IMD) to be implanted to facilitate tissue conductive communication (TCC) between the first IMD and a second IMD implanted within the patient. In some examples, the method includes storing model data that associates patient parameter data and second IMD position data with first IMD positions based on TCC communication performance, receiving patient parameter data indicating one or more anatomical or physiological parameters of the patient, receiving second IMD position data, performing analysis by at least one of comparing the model data to the patient parameter data and the second IMD position data, performing real-time computer simulations, or a combination of comparing and performing simulations, and outputting to a user an indication of the position for the first IMD to be implanted within the patient based on the analysis.

42 Claims, 15 Drawing Sheets

(56) References Cited

U.S. PATENT DOCUMENTS

| | | |
|---|---|---|
| 6,644,321 B1 | 11/2003 | Behm |
| 6,699,200 B2 | 3/2004 | Cao et al. |
| 7,991,467 B2 | 8/2011 | Markowitz et al. |
| 8,515,559 B2 | 8/2013 | Roberts et al. |
| 8,864,676 B2 | 10/2014 | Beasley et al. |
| 8,934,987 B2 | 1/2015 | Stahmann et al. |
| 8,942,818 B2 | 1/2015 | Markowitz et al. |
| 8,983,619 B2 | 3/2015 | Cinbis et al. |
| 2006/0020300 A1 | 1/2006 | Nghiem et al. |
| 2006/0161213 A1 | 7/2006 | Patel |
| 2006/0241732 A1 | 10/2006 | Denker et al. |
| 2007/0123947 A1 | 5/2007 | Wenger et al. |
| 2007/0203546 A1 | 8/2007 | Stone et al. |
| 2008/0269763 A1 | 10/2008 | Bonde et al. |
| 2009/0018599 A1 | 1/2009 | Hastings et al. |
| 2009/0030288 A1 | 1/2009 | Abboud et al. |
| 2009/0253985 A1 | 10/2009 | Shacher et al. |
| 2009/0276020 A1 | 11/2009 | Nee et al. |
| 2009/0318995 A1 | 12/2009 | Keel et al. |
| 2010/0016840 A1 | 1/2010 | Stahmann et al. |
| 2011/0160557 A1 | 6/2011 | Cinbis et al. |
| 2011/0160801 A1 | 6/2011 | Markowitz et al. |
| 2011/0213260 A1* | 9/2011 | Keel .............. A61B 5/04085 600/513 |
| 2012/0095744 A1 | 4/2012 | Rahman et al. |
| 2014/0267662 A1* | 9/2014 | Lampo .............. G06F 19/324 348/77 |
| 2014/0276928 A1 | 9/2014 | Vanderpool et al. |
| 2016/0310031 A1 | 10/2016 | Sarkar |

* cited by examiner

DETERMINING A POSITION FOR AN IMPLANTABLE MEDICAL DEVICE

TECHNICAL FIELD

The disclosure relates to medical device systems and, more particularly, to techniques for determining how to position an implantable medical device inside a patient to, for example, facilitate communication.

BACKGROUND

Various implantable medical devices have been clinically implanted or proposed for therapeutically treating or monitoring one or more physiological conditions of a patient. Such devices may be adapted to monitor or treat conditions or functions relating to heart, muscle, nerve, brain, stomach, endocrine organs or other organs and their related functions. Advances in design and manufacture of miniaturized electronic and sensing devices have enabled development of implantable devices capable of therapeutic as well as diagnostic functions such as pacemakers, cardioverters, defibrillators, biochemical sensors, and pressure sensors, among others. Such devices may be associated with leads to position electrodes or sensors at a desired location, or may be leadless, with the ability to wirelessly transmit data either to another device implanted in the patient or to another device located externally of the patient, or both.

By way of illustrative example, implantable miniature sensors have been proposed and used in blood vessels to measure directly the diastolic, systolic and mean blood pressures, as well as body temperature and cardiac output. As one example, patients with chronic cardiovascular conditions, particularly patients suffering from chronic heart failure, may benefit from the use of implantable sensors adapted to monitor blood pressures. As another example, subcutaneously implantable monitors have been proposed and used to monitor heart rate and rhythm, as well as other physiological parameters, such as patient posture and activity level. Such direct in vivo measurement of physiological parameters may provide significant information to clinicians to facilitate diagnostic and therapeutic decisions. If linked electronically to another implanted therapeutic device (e.g., a pacemaker), the data can be used to facilitate control of that device. Such devices also, or alternatively, may be wirelessly linked to an external receiver.

SUMMARY

In general, this disclosure is directed to techniques for determining a position, e.g., location and/or orientation, for implanting a first implantable medical device (IMD) within a patient. The position for the first IMD may be determined, e.g., by an external programmer or other computing device or system, based on a position of a second IMD that is already implanted within the patient. The position for the first IMD may be determined to facilitate communication, e.g., tissue conductive communication (TCC), between the first IMD and the second IMD.

As one example, the disclosure is directed to a method for identifying a position within a patient for a first implantable medical device (IMD) to be implanted to facilitate tissue conductive communication (TCC) between the first IMD and a second IMD implanted within the patient, the method including storing model data that associates patient parameter data and second IMD position data with first IMD positions based on TCC communication performance. The method further includes receiving patient parameter data indicating one or more anatomical or physiological parameters of the patient and receiving second IMD position data indicating a position of the second IMD within the patient and an orientation of the second IMD within the patient. The method also includes performing analysis by at least one of comparing the model data to the patient parameter data and the second IMD position data, performing real-time computer simulations, or using a combination of comparing the model data to the patient parameter data and the second IMD position data or performing the real-time computer simulations. The method includes outputting to a user an indication of the position for the first IMD to be implanted within the patient based on the analysis.

A method for identifying a position within a patient for a first implantable medical device (IMD) to be implanted to facilitate tissue conductive communication (TCC) between the first IMD and a second IMD implanted within the patient, the method including receiving an image of the second IMD within the patient. The method further includes determining a position of the second IMD within the patient and an orientation of the second IMD within the patient based on the image and storing model data that associates patient parameter data and second IMD position data with first IMD positions based on TCC communication performance. The method also includes receiving patient parameter data indicating one or more anatomical or physiological parameters of the patient and performing analysis by at least one of comparing the model data to the patient parameter data and the second IMD position data, performing real-time computer simulations, or using a combination of comparing the model data to the patient parameter data and the second IMD position data or performing the real-time computer simulations. The method further includes outputting to a user an indication of the position for the first IMD to be implanted within the patient based on the analysis.

As another example, the disclosure is directed to a medical device system for identifying a position within a patient for a first implantable medical device (IMD) to be implanted to facilitate tissue conductive communication (TCC) between the first IMD and a second IMD implanted within the patient, the medical device system including a user interface and processing circuitry configured to store model data that associates patient parameter data and second IMD position data with first IMD positions based on TCC communication performance. The processing circuitry is further configured to receive patient parameter data indicating one or more anatomical or physiological parameters of the patient and receive second IMD position data indicating a position of the second IMD within the patient and an orientation of the second IMD within the patient. The processing circuitry is also configured to perform analysis by at least one of comparing the model data to the patient parameter data and the second IMD position data, performing real-time computer simulations, or using a combination of comparing the model data to the patient parameter data and the second IMD position data or performing the real-time computer simulations. The processing circuitry is further configured to output, via the user interface, an indication of the position for the first IMD to be implanted within the patient based on the analysis.

As another example, the disclosure is directed to a computer-readable medium including instructions for causing at least one programmable processor of a computing device to identify a position within a patient for a first implantable medical device (IMD) to be implanted to facilitate tissue conductive communication (TCC) between the first IMD and a second IMD implanted within the patient by at least storing model data that associates patient parameter data and second IMD position data with first IMD positions based on TCC communication performance; receiving patient parameter data indicating one or more anatomical or physiological parameters of a patient; receiving second IMD position data indicating a position of a second IMD within the patient and an orientation of the second IMD within the patient; performing analysis by at least one of comparing the model data to the patient parameter data and the second IMD position data, performing real-time computer simulations, or using a combination of comparing the model data to the patient parameter data and the second IMD position data or performing the real-time computer simulations; and outputting to a user an indication of the position for the first IMD to be implanted within the patient based on the analysis.

As another example, the disclosure is directed to a method for identifying a position within a patient for a first implantable medical device (IMD) to be implanted to facilitate tissue conductive communication (TCC) between the first IMD and a second IMD implanted within the patient, the method including storing model data that associates patient parameter data and second IMD position data with first IMD positions based on TCC communication performance. The method also includes receiving patient parameter data including a height of the patient, a weight of the patient, and a chest circumference of the patient and receiving an image of the second IMD within the patient. The method further includes determining a position of the second IMD within the patient and an orientation of the second IMD within the patient based on the image and performing analysis by at least one of comparing the model data to the patient parameter data and the second IMD position data, performing real-time computer simulations, or using a combination of comparing the model data to the patient parameter data and the second IMD position data or performing the real-time computer simulations. The method includes outputting to a user an indication of the position for the first IMD to be implanted within the patient based on the analysis.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

BRIEF DESCRIPTION OF DRAWINGS

The details of one or more examples of this disclosure are set forth in the accompanying drawings and the description below. Other features, objects, and advantages of this disclosure will be apparent from the description and drawings, and from the claims.

The drawings and the description provided herein illustrate and describe various examples of the inventive methods, devices, and systems of the present disclosure. However, the methods, devices, and systems of the present disclosure are not limited to the specific examples as illustrated and described herein, and other examples and variations of the methods, devices, and systems of the present disclosure, as would be understood by one of ordinary skill in the art, are contemplated as being within the scope of the present application.

DETAILED DESCRIPTION

Figure 1A:
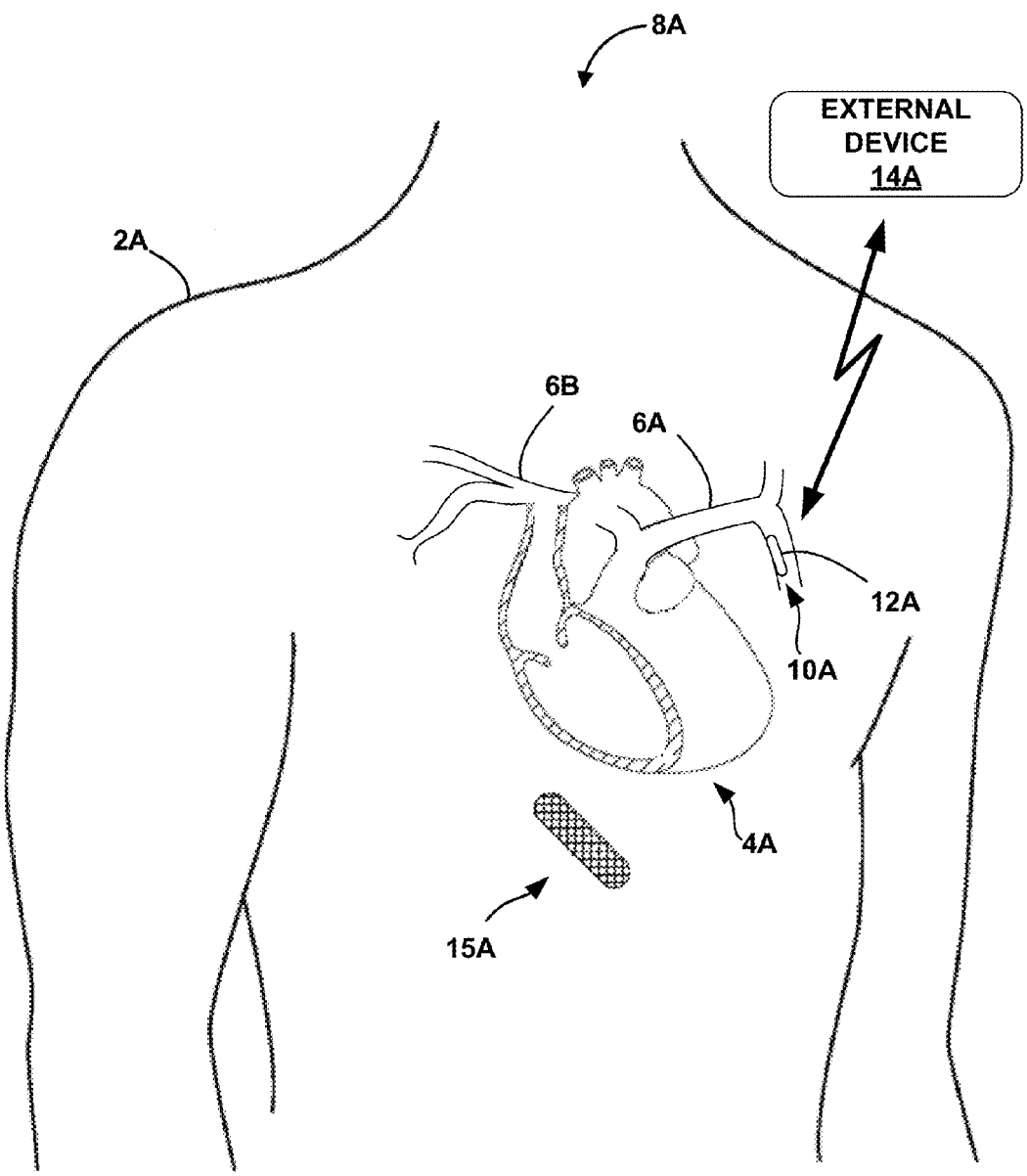
FIG. 1A is a conceptual drawing illustrating an example medical device system in conjunction with a patient.

FIG. 1A is a conceptual drawing illustrating an example medical device system 8A in conjunction with a patient 2A. Medical device system 8A is an example of a medical device system configured to implement the techniques described herein that include communication between implanted medical devices and for which a position for implanting one of the implantable medical devices may be indicated. In the illustrated example, medical device system 8A includes an implantable medical device (IMD) 15A, also referred to as implantable monitoring device 15A or an implantable hub device, in communication with external device 14A. Medical device system 8A also includes an implantable sensor assembly 10A that includes an implantable pressure sensing device 12A, also referred to as sensor device 12A. For purposes of this description, knowledge of cardiovascular anatomy is presumed and details are omitted except to the extent necessary or desirable to explain the context of the techniques of this disclosure.

As shown in FIG. 1A, implantable sensor assembly 10A may be implanted within pulmonary artery 6A of heart 4A. In some examples, pulmonary artery 6A of heart 4A may comprise a left pulmonary artery, and pulmonary artery 6B may comprise a right pulmonary artery. Although FIG. 1A depicts sensing device 12A positioned in a descending branch of the left pulmonary artery, sensing device 12A may positioned elsewhere with left pulmonary artery 6A, in right pulmonary artery 6B, or any suitable region of the patient's cardiovascular system. For the sake of clarity, a fixation assembly for sensor assembly 10A is not depicted in FIG. 1A. A suitable fixation assembly configured to secure sensor assembly 10A within pulmonary artery 6A will be discussed below with respect to FIG. 2.

Intra-body communication between multiple implants may be utilized to send or receive data from very small active sensors or pulse generators. The intra-body communication may be accomplished by a tissue conductance communication (TCC) protocol, e.g., a communication protocol operating at a relatively low frequency across the conductive tissues of the body. TCC may also refer to trans-conductance communication. For example, a small active pressure sensor implanted in the pulmonary artery, e.g., sensor devices 12A and 12B, may relay pressure data to an insertable cardiac monitor (ICM), e.g., IMD 15A, or a pacemaker or implantable cardioverter-defibrillator (ICD), e.g., IMD 15B of FIG. 1B, which may then relay the data to a base station, e.g., external device 14A or 14B, for active monitoring and tracking for patients with various physiological disease states, such as heart failure patients. The methods of this disclosure may apply to a wide range of disease states and/or to general health monitoring.

In some examples, instead of or in addition to pressure sensing device 12A, an IMD that communicates via TCC is a pacemaker configured to deliver cardiac pacing to treat one or more of bradycardia, tachycardia, or heart failure. For example, left heart pacing may be used to manage heart failure in a patient with an existing ICD by implanting a leadless pacemaker in the left ventricle and using TCC to trigger the pace output of the left heart leadless pacemaker at an appropriate time during the cardiac cycle in order to improve cardiac output. In some examples, an ICD may be configured to trigger a pacemaker in a chamber of heart 4A to deliver pacing for bradycardia, anti-tachycardia pacing (ATP), or post-shock pacing. The ICD may be configured to coordinate anti-tachycardia therapy by communicating via TCC with other devices.

In the illustrated example, IMD 15A is an ICM capable of sensing and recording cardiac electrogram (EGM) signals from a position outside of heart 4A via electrodes, and will be referred to as ICM 15A hereafter. In some examples, ICM 15A includes or is coupled to one or more additional sensors, such as accelerometers, that generate one or more signals that vary based on patient motion and/or posture, blood flow, or respiration. ICM 15A may monitor a physiological parameter indicative of patient state, such as posture, heart rate, activity level, heart rate, respiration rate, and/or other parameters. ICM 15A may include processing circuitry to analyze measured parameters. ICM 15A may be implanted outside of the thorax of patient 2A, e.g., subcutaneously or submuscularly, such as the pectoral location illustrated in FIG. 1A. ICM 15A may be positioned near the sternum near or just below the level of heart 4A. In some examples, ICM 15A may take the form of a Reveal LINQ™ ICM, available from Medtronic plc, of Dublin, Ireland.

Sensor device 12A may include pressure sensing circuitry configured to measure the cardiovascular pressure of patient 2A. Sensor device 12A may measure and transmit the cardiovascular pressure of patient 2A to ICM 15A. ICM 15A may transmit posture data, and other physiological parameter data acquired by ICM 15A, to external device 14A. ICM 15A may also transmit cardiovascular pressure measurements received from sensor device 12A to external device 14A. For example, ICM 15A may transmit any data described herein related to cardiovascular pressure, posture, heart rate, activity level, respiration rate, and/or other physiological parameters to external device 14A. For purposes of this disclosure, a cardiovascular pressure measurement may include one or more numerical values such as a systolic value and/or a diastolic value, a waveform of the cardiovascular pressure, and/or any other data relating to cardiovascular pressure.

External device 14A may be a computing device, e.g., used in a home, ambulatory, clinic, or hospital setting, to communicate with ICM 15A via wireless telemetry. External device 14A may be coupled to a remote patient monitoring system, such as Carelink®, available from Medtronic plc, of Dublin, Ireland. External device 14A may be, as examples, a programmer, external monitor, or consumer device, e.g., smart phone. In some examples, external device 14A may receive time-stamped data from ICM 15A. The time-stamped data may include measurements of cardiovascular pressure, the posture of patient 2A, and other parameters such as heart rate and respiration rate.

External device 14A may be used to program commands or operating parameters into ICM 15A and/or sensor device 12A for controlling their functioning, e.g., when configured as a programmer for ICM 15A and/or sensor device 12A. External device 14A may be used to interrogate ICM 15A to retrieve data, including device operational data as well as physiological data accumulated in a memory of ICM 15A, which may have been collected by ICM 15A, or collected by sensor device 12A and communicated to ICM 15A. The interrogation may be automatic, e.g., according to a schedule, or in response to a remote or local user command. Examples of communication techniques used by ICM 15A and external device 14A include radiofrequency (RF) telemetry, which may be an RF link established via Bluetooth, WiFi, or medical implant communication service (MICS).

Medical device system 8A is an example of a medical device system in which implantable medical devices communicate with each other and one or more external devices. Each of sensor device 12A, external device 14A, and ICM 15A may communicate through TCC with other devices in medical device system 8A. The positions of sensor device 12A and ICM 15A may affect the communication between the devices of medical device system 8A. For example, the position of ICM 15A, e.g., the location and orientation, may affect the signal strength, noise, and frequency response of signals transmitted between ICM 15A and sensor device 12A.

For example, the orientation of a first vector formed by a combination of electrodes used by ICM 15A for TCC communication relative to a second vector formed by a combination of electrodes used by sensor device 12A for TCC communication may affect the signal strength, noise, and frequency response of signals transmitted between ICM 15A and sensor device 12A. Similarly, types of patient tissue between ICM 15A and sensor device 12A may affect the signal strength, noise, and frequency response of signals transmitted between ICM 15A and sensor device 12A. The position, e.g., location and orientation, of sensor device 12A may be largely constrained by the patient's anatomy at the relatively deep, e.g., intravascular, location at which it is implanted. Consequently, according to the techniques of this disclosure, processing circuitry of one or more devices, e.g., external device 14A or another computing device, may determine an implant location for ICM 15A to provide adequate signal strength and frequency response of signals, with relatively lower noise.

In accordance with the techniques of this disclosure, external device 14A or another computing device may be configured to identify a position within patient 2A for a first device to be implanted to facilitate TCC between the first device and a second device that is already implanted within patient 2A. In some examples, sensor device 12A may already be implanted within patient 2A, and a position of ICM 15A within patient 2A may be identified. Alternatively, ICM 15A may already be implanted within patient 2A, and a position of sensor device 12A within patient 2A may be identified. External device 14A or the other computing device may be configured to store model data associating patient parameter data and second IMD position data with first IMD positions based on TCC communication performance.

The TCC communication performance of the model data may be based on experimental data from other patients. The experimental data may include the communication characteristics and IMD positions from other patients with implanted devices. The model data may also include the computer simulations of TCC communication between devices in a patient. The computer simulations may include computational modeling of TCC communication using a variety of realistic patient torso models. The computer simulations may be based on the conductivity and permittivity of organs and tissue in a patient. The processing circuitry of external device 14 may be configured to store the simulated results in an analysis module, a database, and/or a lookup table.

In some examples, the computer simulations may include numerous torso models for different shapes and sizes of patients, including women, men, adults, children, and elderly patients. Some of the torso models may represent different postures and other characteristics. The model data may include thousands or millions of computer simulations of various device positions and orientations within each of the torso models. The model data may include, e.g., for each of the various positions and orientations, signal strengths, voltage gradients, signal to noise ratios, and other results of the computer simulations.

In some examples, the computer simulations may model and simulate the specific electrical properties of the tissue, bone, and organs of a patient. Alternatively or additionally, the computer simulations may assume that the tissue of the patient has a constant electrical property that is the average of the tissue, bone, and organs of the patient. The assumed electrical properties may be based on the locations of the device(s) within the patient. The model data may allow for interpolation if the actual patient parameter data, device position, and device orientation do not match any of the models or computer simulations. For example, if the actual patient characteristics are halfway between two models, then the system may determine a recommended position for each model and output a recommended position that is halfway between the two recommended positions. As a general example, the model data may include simulations for a tall person and for a short person, but the actual patient may be medium height. In some examples, the system could average the two recommended positions and output the average position.

The techniques of this disclosure may include software implemented on external device 14A or another computing device that acts as an interactive pre-operative implant planning guide to help a clinician choose an implant location for a first device such that the most reliable communication between devices is achieved. For example, after a pressure sensor is implanted in the pulmonary artery, an anterior-posterior fluoroscopic image of the patient with the sensor may be imported in the software to determine the location and/or orientation of the pressure sensor within the patient. The software may also prompt for potential patient attributes such as height and chest circumference. The orientation and the relative position of the pressure sensor implant location may be identified in a fluoroscopic image, which then, along with patient attribute data, may be used to compare against a simulation database that contains a wide variety of patient sizes and implant locations. In addition or in the alternative, the processing circuitry of external device 14A may be configured to simulate the communication between the first device and the pressure sensor implant at one or more possible positions for the first device. The closest matching scenario in the simulation database may be used to identify an ideal implant location and orientation for the other device to provide a desirable signal strength and communication reliability between the devices within the body. In some examples, external device 14A may be configured to apply an interpolation or a transfer function based on the model data. If the model data includes several close data points, external device 14A may average or weigh the data points to interpolate a location for the first IMD.

Depending on the type of device to be implanted, device placement and orientation may be optimized (i.e., selected) for multiple parameters. For example, if the device to be implanted is an implantable loop recorder, the placement and orientation recommendation could be selected to provide adequate TCC signal strength and cardiac electrogram signal sensing, e.g., amplitude of R-waves or other features and minimal noise, for monitoring of the heart. In some examples, the IMD to be implanted may be configured to monitor behavior of the heart. The recommended position for the IMD may be based on the quantitative measurement (e.g., the strength) of electrocardiogram (ECG) signals received by an array of electrodes positioned on the patient. The processing circuitry may analyze the electrode data to determine which pair or other grouping of electrodes received the strongest ECG signal. The processing circuitry may determine a recommended position and orientation to implant the IMD within the patient based on the ECG signal as well as the expected TCC performance.

The model data may include an analysis module, a lookup table, a database, and/or an algorithm that relates the position of the second device and the characteristics of patient 2A with possible positions of the first IMD. The model data may be stored in a memory device of external device 14A and/or another computing device. In some examples, the model data may be stored in a database, and external device 14A may execute a query on the database based on patient parameter data and position data for the IMD that is already implanted. A cloud-based computing system may be configured to store the model data and receive a query from external device 14A, which may be located in the clinician's office or with the patient. External device 14A may have a network connection to the cloud-based database and may transmit a query that includes the patient parameter data and position data. In some examples, the cloud-based database may have greater storage capacity, and it may be easier to update the cloud-based database than to update numerous databases stored on external devices in clinician offices. In some examples, the model data may include an analysis module and/or a lookup table associating IMD locations, patient parameter data, and TCC communication performance. The analysis module and/or lookup table may include additional variables and IMD types.

External device 14A or the other computing device may be configured to receive patient parameter data indicating one or more anatomical or physiological parameters of patient 2A. The patient parameter data may, for example, include the height, weight, chest circumference, gender, and/or age of patient 2A. A clinician may enter the patient parameter data, or the patient parameter data may be located in medical records for the patient. A clinician may also use medical records for patient 2A to enter the patient parameter data into external device 14A.

External device 14A or the other computing device may also be configured to receive second IMD position data indicating a position of the second IMD, e.g., location and orientation, within patient 2A. The second IMD position data may include or be derived from a fluoroscopic image of patient 2A showing the second IMD within patient 2A and/or an anterior-posterior image of patient 2A showing the second IMD within patient 2A. In some examples, processing circuitry, e.g., of external device 14A or another computing device, determines the position and/or orientation of the second IMD within patient 2A based on the position of the second IMD within patient 2A in the image. The processing circuitry of external device 14A may be configured to recognize automatically or semi-automatically the position of the second IMD. In some examples, a user may mark the position of the second IMD on the image before or after uploading the image. The processing circuitry of external device 14A may be configured to recognize the mark on the image indicating the position of the second IMD within patient 2A. In some examples, a clinician may load the image of patient 2A into the computing device for analysis by the processing circuitry. In some examples, a clinician may input the position and orientation of the second IMD to external device 14A using a user interface with a graphical representation of patient 2A.

The clinician may also input the position of the second IMD via a list of locations in patient 2A. The list of locations may correspond to a predefined list of common use scenarios. For example, the processing circuitry may be configured to allow the clinician to select from a list of left pulmonary implant positions that best represents the position of the second IMD in patient 2A. Other common use scenarios may include subcutaneous positions, positions inside the heart, and/or other positions within patient 2A.

External device 14A or the other computing device may be further configured to compare the model data to the patient parameter data and the second IMD position data. In some examples, the model data may include an analysis module and/or a lookup table or other data structure that associates implant positions for the first IMD with various combinations of values for the patient parameter data and the second IMD position data. External device 14A or the other computing device may also be configured to output to a user an indication of the position for the first IMD to be implanted within patient 2A based on the comparison of the model data to the patient parameter data and the second IMD position data. The indication may include a display of the position for the first IMD on a graphical representation of patient 2A. The indication may also include position data such as the depth of the position for the first IMD beneath the skin of patient 2A and/or the distance from or location relative to the sternum or another anatomical structure of patient 2A.

By identifying a position for the first IMD before the implantation of the first IMD, the transmission and receipt of TCC signals between the first IMD and the second IMD may be improved. The comparison of the model data to patient parameter data and the second IMD position data may result in identifying a position for the first IMD that allows for better TCC quality, as compared to methods of identifying an implantation position for the first IMD that do not consider such factors. In some examples, external device 14A may be configured to compare the model data in addition to or in the alternative to performing real-time computer simulations based on torso model(s) and the conductivity and permittivity of organs and tissue in patient 2A.

In some examples, the signal strength of TCC may be dependent on a number of parameters. One significant parameter may depend on the effective dipole orientation between the transmit/receive electrodes on both devices. Poor alignment between the pair of devices may result in poor signal strength and potentially frequent communication dropouts. Often times, the position of one of the implants may be largely determined due to the anatomy of a patient, such as the position of a pressure sensor in the pulmonary artery.

Figure 1B:
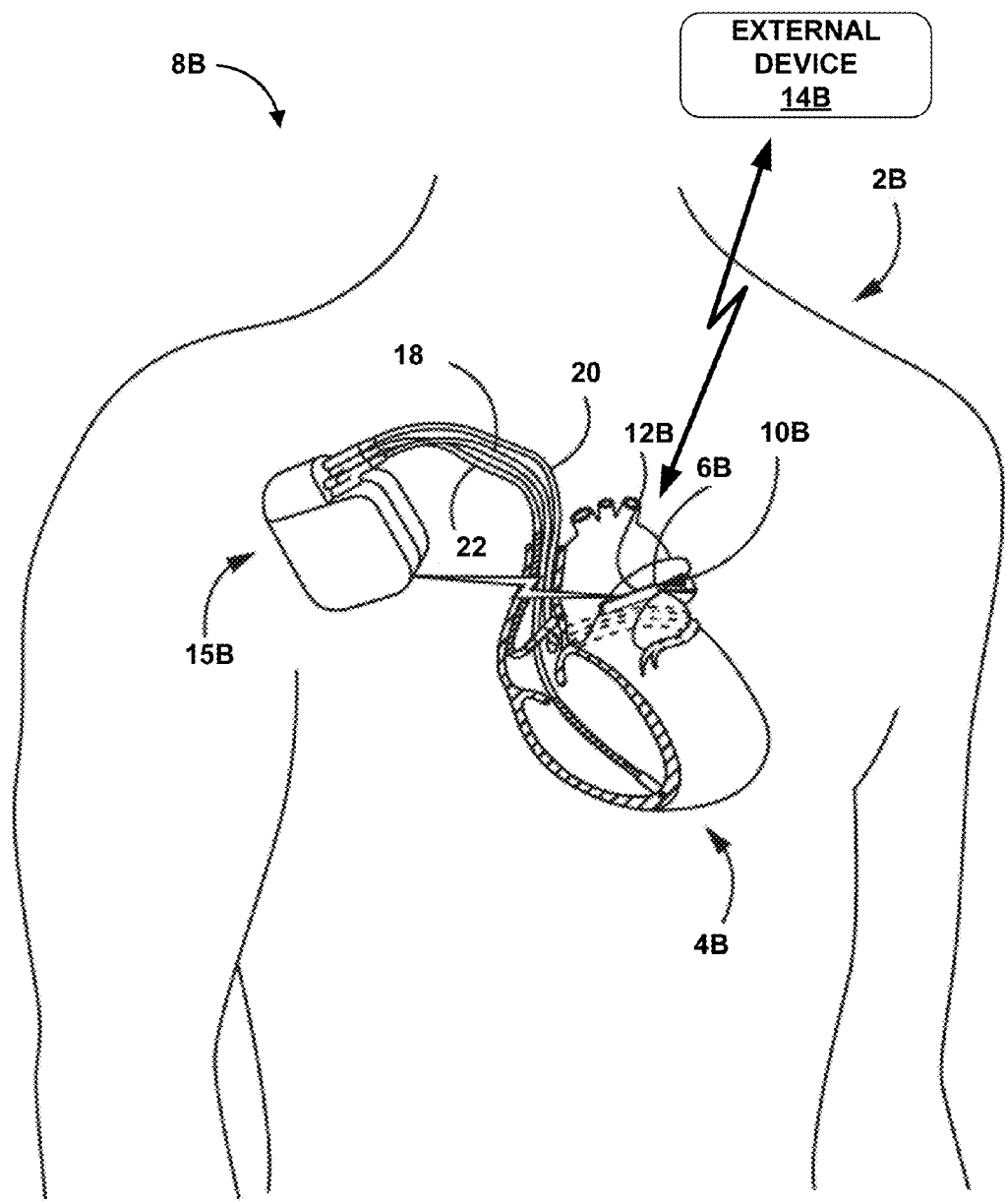
FIG. 1B is a conceptual diagram illustrating another example medical device system in conjunction with a patient.

FIG. 1B is a conceptual diagram illustrating another example medical device system 8B in conjunction with a patient 2B. In the illustrated example, medical device system 8B includes a sensor assembly 10B implanted, for example, in the patient's pulmonary artery 6B through which blood flows from the heart 4B to the lungs, and another IMD 15B. Medical device system 8B is another example of a medical device system configured to implement the techniques described herein that include communication between implanted medical devices and for which a position for implanting one of the implantable medical devices may be indicated. The sensor device 12B, IMD 15B, and external device 14B in FIG. 1B may provide substantially similar functionality, e.g., with respect to the techniques described herein for monitoring cardiovascular pressure and other physiological parameters of a patient, as the like numbered device described above with respect to FIG. 1A.

IMD 15B may have one or more leads 18, 20, 22 including electrodes that are placed on or near selected portions of the cardiac anatomy in order to perform the functions of IMD 15B as is well known to those skilled in the art. For example, IMD 15B may be configured to sense and record physiological signals, such as cardiac EGM signals, via the electrodes on leads 18, 20, 22. IMD 15B may also be configured to deliver therapeutic signals, such as pacing pulses, cardioversion shocks, or defibrillation shocks, to heart 4B via the electrodes. In the illustrated example, IMD 15B may be a pacemaker and/or defibrillator.

In some examples, this disclosure may refer to IMD 15B, particularly with respect to its functionality as part of a medical device system that monitors cardiovascular pressure and other physiological parameters of patient 2B and communicates with sensor device 12B, as an implantable monitoring device or implantable hub device. In some examples, IMD 15B includes or is coupled to one or more additional sensors, such as accelerometers, that generate one or more signals that vary based on patient motion and/or posture, blood flow, or respiration. IMD 15B may monitor a physiological parameter indicative of patient state, such as posture, heart rate, activity level, heart rate, and/or respiration rate.

IMD 15B also may have wireless capability to receive and transmit, by telemetry, signals relating to operation of the device, and to receive programming commands. IMD 15B may communicate wirelessly to an external device such as external device 14B or to another implanted device such as a sensor device 12B of the sensor assembly 10B. For sake of clarity, sensor assembly 10B is shown without a fixation assembly in FIG. 1B. The sensor device 12B also may communicate wirelessly with external device 14B to provide in vivo data for selected physiological parameters to an external site to inform clinicians of the patient's status. In some examples, sensor device 12B may communicate wirelessly and directly with external device 14B, rather than communicating with external device 14B through IMD 15B. In a similar way, sensor device 12A of FIG. 1A may communicate wirelessly and directly with external device 14A.

Medical device system 8B is an example of a medical device system in which implantable medical devices communicate with each other and one or more external devices. Similar to the processing circuitry of external device 14A of FIG. 1A, the processing circuitry of external device 14B may be configured to identify a position for IMD 15B before the implantation of IMD 15B. The processing circuitry of external device 14B may be configured to identify a position for IMD 15B based on position data for sensor device 12B and parameter data for patient 2B, in the same manner to that described above with respect to 14A of FIG. 1A. In some examples, similar to the processing circuitry of external device 14A of FIG. 1A, the processing circuitry of external device 14B may be configured to identify a position for sensor device 12B before implantation of sensor device 12B based on position data for IMD 15B.

Although described herein primarily in the context of implantable medical devices monitoring cardiovascular pressure, such as those illustrated in FIGS. 1A and 1B, a medical device system that implements the techniques described in this disclosure may additionally or alternatively include any of a variety of implanted or external medical devices for which intra-device communication may be improved by identifying an implantation position for one of the devices using the techniques of this disclosure. Instead of, or in addition to the pressure sensing devices, ICMs, and implantable pacemaker-cardioverter-defibrillators described above with respect to FIGS. 1A and 1B, a medical device system 4 may include an extravascular defibrillator (e.g., a subcutaneous ICD), mechanical circulatory support devices, and/or a leadless (e.g., intracardiac) pacemaker, as examples. Moreover, such techniques may be used in systems that additionally or alternatively include devices for monitoring or treating non-cardiac conditions, such as spinal cord stimulators, deep brain stimulators, gastric stimulators, drug delivery devices, or other devices.

Figure 2:
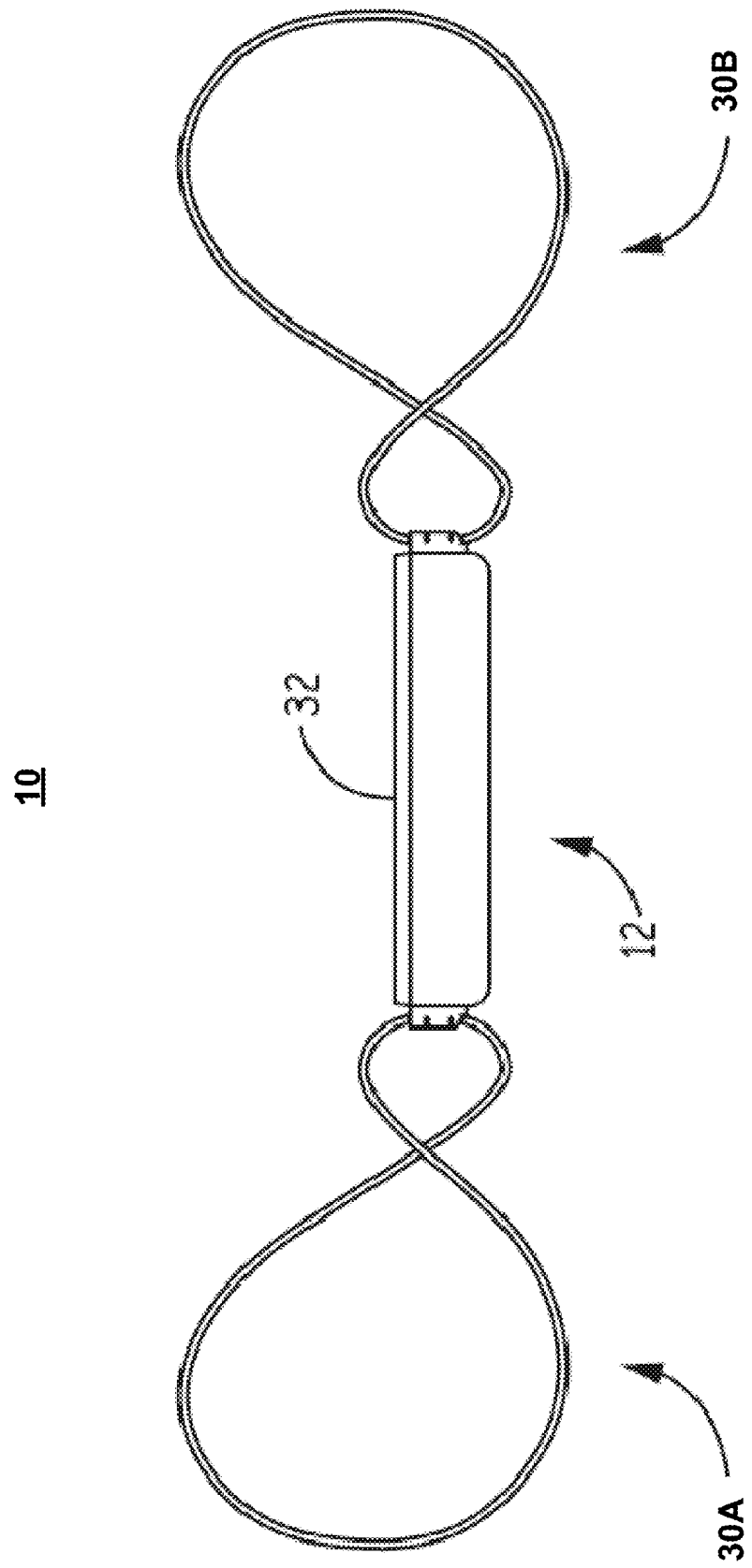
FIG. 2 illustrates a side profile view of an example sensor assembly.

FIG. 2 illustrates an example of a sensor assembly adapted for minimally invasive placement in a patient's blood vessel, the assembly being shown in its expanded, deployment configuration. A side profile view of an example configuration of sensor assembly 10 is depicted. Each of sensor assemblies 10 includes a sensor 12 coupled to fixation members 30A, 30B (collectively "fixation assembly 30"). The fixation assembly 30 and sensor 12 are arranged to enable the sensor assembly 10 to be provided in a delivery configuration that enables it to be navigated to an implant location where it can be deployed into the deployment configuration. As described in this disclosure, it should be understood that the delivery configuration defines a pitch, width or diameter that is narrower, in relation to the deployment configuration, along a common plane. Upon release, the fixation assembly expands into the deployment configuration so as to be in physical contact with the wall of the blood vessel to maintain the positional integrity of sensor device 12. In one example, the fixation assembly will engage the interior wall of the vessel defining the blood flow lumen.

The sensor device 12 is attached to the fixation assembly 30 in a manner such that the sensing element 32 of the sensor device 12 is spaced from the wall of the vascular lumen to minimize adverse obstruction to blood flow through the lumen and to position the sensing element 32 of the sensor device 12 to be fully exposed to the blood in the vessel, without obstruction from the housing of the sensor or the vessel wall.

Figure 3:
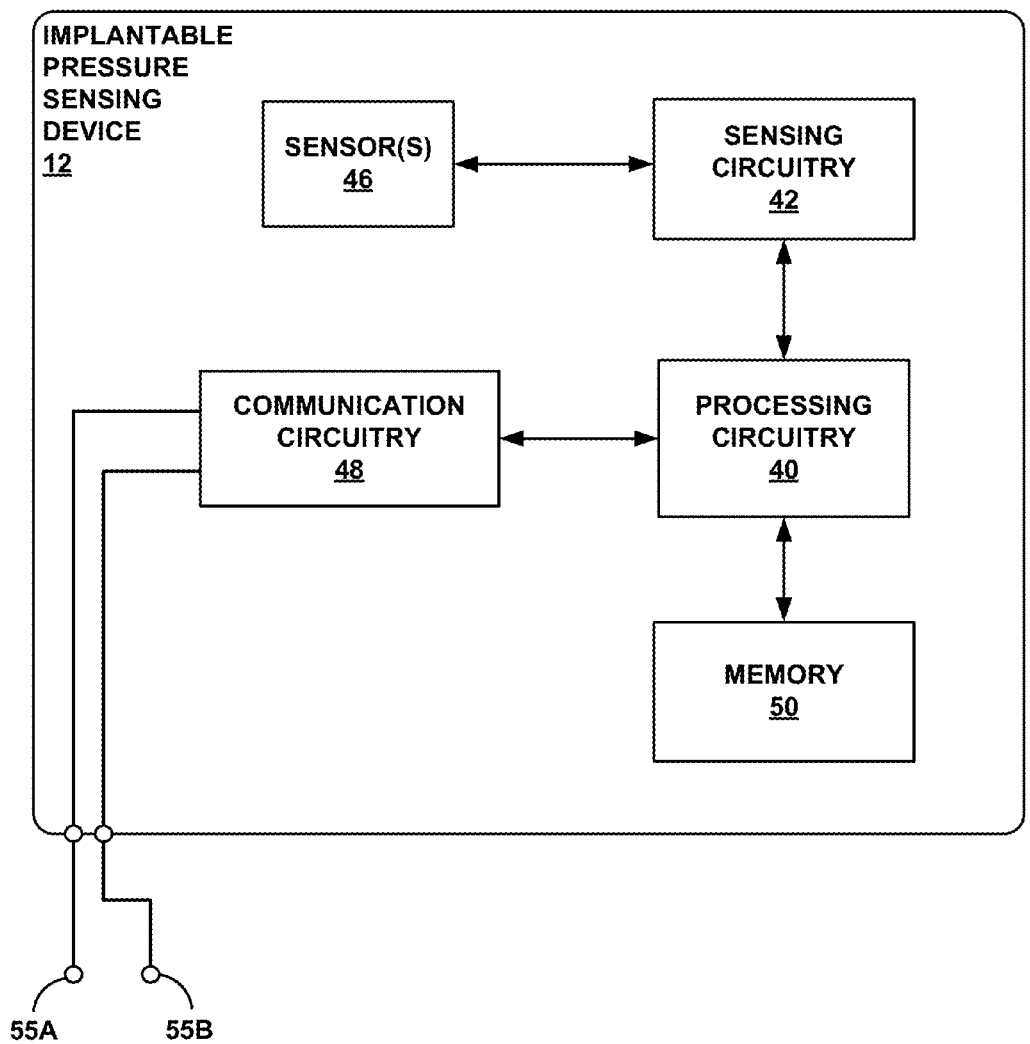
FIG. 3 is a functional block diagram illustrating an example configuration of implantable pressure sensing device.

FIG. 3 is a functional block diagram illustrating an example configuration of implantable pressure sensing device 12, hereinafter called "sensor 12" or "sensing device 12." Sensing device 12 may correspond to any of sensor device 12A in FIG. 1A, sensor device 12B in FIG. 1B, sensor device 12 in FIG. 2, or another pressure sensing device configured to implement the techniques for measuring cardiovascular pressure as described in this disclosure. In the illustrated example, sensing device 12 includes processing circuitry 40 and an associated memory 50, sensing circuitry 42, one or more sensors 46, and communication circuitry 48. However, sensing device 12 need not include all of these components, or may include additional components.

Memory 50 includes computer-readable instructions that, when executed by processing circuitry 40, cause sensing device 12 and processing circuitry 40 to perform various functions attributed to sensing device 12 and processing circuitry 40 herein (e.g., determining time of day, comparing time of day to a predetermined window, causing communication circuitry 48 to receive triggering signals from another device, causing communication circuitry 48 to transmit cardiovascular pressure measurements to the other device). Memory 50 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. Memory 50 may store threshold(s) for time of day and other parameters. Memory 50 may also store data indicating cardiovascular pressure measurements.

Processing circuitry 40 may include fixed function circuitry and/or programmable processing circuitry. Processing circuitry 40 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 40 may include multiple components, such as any combination of one or more microprocessors, one or more controllers, one or more DSPs, one or more ASICs, or one or more FPGAs, as well as other discrete or integrated logic circuitry. The functions attributed to processing circuitry 40 herein may be embodied as software, firmware, hardware or any combination thereof.

Sensing circuitry 42 may monitor signals from sensors 46, which may include pressure sensors. In some examples, sensing circuitry 42 may sense or detect physiological parameters such as blood pressure in the cardiovascular system of a patient. In some examples, sensing device 12 may be implanted in a pulmonary artery of the patient.

In some examples, sensors 46 include one or more pressure sensors that transduce one or more signals indicative of blood pressure, and processing circuitry 40 determines one or more patient parameter values based on the pressure signals. A capacitive pressure sensor is one example of a sensor for transducing pressure. Other example pressure sensors include piezoresistive, piezoelectric, electromagnetic, or optical pressure sensors. Patient parameter values determined based on pressure may include, as examples, systolic or diastolic pressure values, such as pulmonary artery diastolic pressure values, or other pulmonary artery pressure values.

Communication circuitry 48 includes any suitable hardware, firmware, software or any combination thereof for communicating with another device, such as IMD 15 or another IMD or sensor, or external device 14. In some examples, communication circuitry 48 may communicate with a local external device, and processing circuitry 40 may communicate with a networked computing device via the local external device and a computer network, such as the Medtronic CareLink® Network developed by Medtronic, plc, of Dublin, Ireland. In the illustrated example, communication circuitry 48 is coupled to electrodes 55A and 55B and configured for TCC communication, e.g., with IMD 15, via the electrodes. In some examples, electrodes 55A and 55B may be integral with a housing of implantable pressure sensing device 12, and/or may take the form of one or more of the fixation elements, e.g., fixation elements 30, of an implantable sensor assembly 10. In some examples, communication circuitry 48 may additionally or alternatively be configured for RF communication via an antenna (not shown).

Communication circuitry 48 may be configured to receive a triggering signal from another device, e.g., IMD 15. The triggering signal may cause processing circuitry 40 to control sensing circuitry 42 and sensor(s) 46 to transduce a cardiovascular pressure signal to measure cardiovascular pressure. Communication circuitry 48 may be further configured to transmit the cardiovascular pressure measurements and/or a portion of the pressure signal waveform to another device, e.g., IMD 15.

Figure 4:
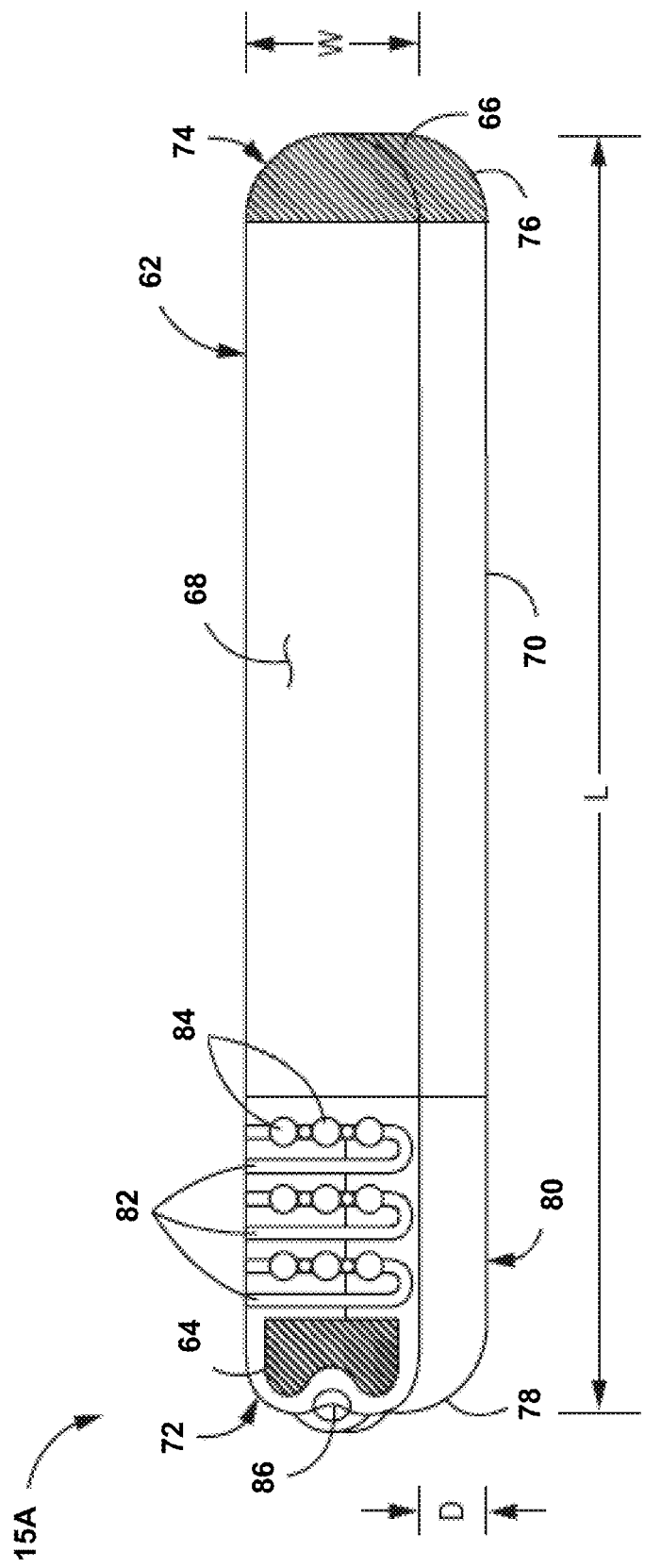
FIG. 4 is a conceptual drawing illustrating an example configuration of an insertable cardiac monitor (ICM).

FIG. 4 is a conceptual drawing illustrating an example configuration of ICM 15A of FIG. 1A. In the example shown in FIG. 4, ICM 15A may be embodied as a monitoring device having housing 62, proximal electrode 64 and distal electrode 66. Housing 62 may further comprise first major surface 68, second major surface 70, proximal end 72, and distal end 74. Housing 62 encloses electronic circuitry located inside the ICM 15A and protects the circuitry contained therein from body fluids. Electrical feedthroughs provide electrical connection of electrodes 64 and 66.

In the example shown in FIG. 4, ICM 15A is defined by a length L, a width W and thickness or depth D and is in the form of an elongated rectangular prism wherein the length L is much larger than the width W, which in turn is larger than the depth D. In one example, the geometry of the ICM 15A—in particular a width W greater than the depth D—is selected to allow ICM 15A to be inserted under the skin of the patient using a minimally invasive procedure and to remain in the desired orientation during insertion. For example, the device shown in FIG. 4 includes radial asymmetries (notably, the rectangular shape) along the longitudinal axis that maintains the device in the proper orientation following insertion. For example, in one example the spacing between proximal electrode 64 and distal electrode 66 may range from thirty millimeters (mm) to fifty-five mm, thirty-five mm to fifty-five mm, and from forty mm to fifty-five mm and may be any range or individual spacing from twenty-five mm to sixty mm. In addition, ICM 15A may have a length L that ranges from thirty mm to about seventy mm. In other examples, the length L may range from forty mm to sixty mm, forty-five mm to sixty mm and may be any length or range of lengths between about thirty mm and about seventy mm. In addition, the width W of major surface 68 may range from three mm to ten mm and may be any single or range of widths between three mm and ten mm. The thickness of depth D of ICM 15A may range from two mm to nine mm. In other examples, the depth D of ICM 15A may range from two mm to five mm and may be any single or range of depths from two mm to nine mm. In addition, ICM 15A according to an example of the present disclosure is has a geometry and size designed for ease of implant and patient comfort. Examples of ICM 15A described in this disclosure may have a volume of three cubic centimeters (cm) or less, one-and-a-half cubic cm or less or any volume between three and one-and-a-half cubic centimeters. In addition, in the example shown in FIG. 4, proximal end 72 and distal end 74 are rounded to reduce discomfort and irritation to surrounding tissue once inserted under the skin of the patient. In some examples, ICM 15A, including instrument and method for inserting ICM 15A is configured as described, for example, in U.S. Patent Publication No. 2014/0276928, incorporated herein by reference in its entirety. In some examples, ICM 15A is configured as described, for example, in U.S. Patent Publication No. 2016/0310031, incorporated herein by reference.

In the example shown in FIG. 4, once inserted within the patient, the first major surface 68 faces outward, toward the skin of the patient while the second major surface 70 is located opposite the first major surface 68. Consequently, the first and second major surfaces may face in directions along a sagittal axis of patient 2A (see FIG. 1A), and this orientation may be consistently achieved upon implantation due to the dimensions of ICM 15A. Additionally, an accelerometer, or axis of an accelerometer, may be oriented along the sagittal axis.

Proximal electrode 64 and distal electrode 66 are used to sense cardiac signals, e.g. ECG signals, intra-thoracically or extra-thoracically, which may be sub-muscularly or subcutaneously. ECG signals may be stored in a memory of the ICM 15A, and ECG data may be transmitted via integrated antenna 82 to another medical device, which may be another implantable device or an external device, such as external device 14A. In some example, electrodes 64 and 66 may additionally or alternatively be used for sensing any biopotential signal of interest, which may be, for example, an EGM, electroencephalogram (EEG), electromyogram (EMG), or a nerve signal, from any implanted location.

In the example shown in FIG. 4, proximal electrode 64 is in close proximity to the proximal end 72 and distal electrode 66 is in close proximity to distal end 74. In this example, distal electrode 66 is not limited to a flattened, outward facing surface, but may extend from first major surface 68 around rounded edges 76 and/or end surface 78 and onto the second major surface 70 so that the electrode 66 has a three-dimensional curved configuration. In the example shown in FIG. 4, proximal electrode 64 is located on first major surface 68 and is substantially flat, outward facing. However, in other examples proximal electrode 64 may utilize the three-dimensional curved configuration of distal electrode 66, providing a three-dimensional proximal electrode (not shown in this example). Similarly, in other examples distal electrode 66 may utilize a substantially flat, outward facing electrode located on first major surface 68 similar to that shown with respect to proximal electrode 64. The various electrode configurations allow for configurations in which proximal electrode 64 and distal electrode 66 are located on both first major surface 68 and second major surface 70. In other configurations, such as that shown in FIG. 4, only one of proximal electrode 64 and distal electrode 66 is located on both major surfaces 68 and 70, and in still other configurations both proximal electrode 64 and distal electrode 66 are located on one of the first major surface 68 or the second major surface 70 (i.e., proximal electrode 64 located on first major surface 68 while distal electrode 66 is located on second major surface 70). In another example, ICM 15A may include electrodes on both major surface 68 and 70 at or near the proximal and distal ends of the device, such that a total of four electrodes are included on ICM 15A. Electrodes 64 and 66 may be formed of a plurality of different types of biocompatible conductive material, e.g. stainless steel, titanium, platinum, iridium, or alloys thereof, and may utilize one or more coatings such as titanium nitride or fractal titanium nitride.

In the example shown in FIG. 4, proximal end 72 includes a header assembly 80 that includes one or more of proximal electrode 64, integrated antenna 82, anti-migration projections 84, and/or suture hole 86. Integrated antenna 82 is located on the same major surface (i.e., first major surface 68) as proximal electrode 64 and is also included as part of header assembly 80. Integrated antenna 82 allows ICM 15A to transmit and/or receive data. In other examples, integrated antenna 82 may be formed on the opposite major surface as proximal electrode 64, or may be incorporated within the housing 62 of ICM 15A. In the example shown in FIG. 4, anti-migration projections 84 are located adjacent to integrated antenna 82 and protrude away from first major surface 68 to prevent longitudinal movement of the device. In the example shown in FIG. 4 anti-migration projections 84 includes a plurality (e.g., nine) small bumps or protrusions extending away from first major surface 68. As discussed above, in other examples anti-migration projections 84 may be located on the opposite major surface as proximal electrode 64 and/or integrated antenna 82. In addition, in the example shown in FIG. 4 header assembly 80 includes suture hole 86, which provides another means of securing ICM 15A to the patient to prevent movement following insert. In the example shown, suture hole 86 is located adjacent to proximal electrode 64. In one example, header assembly 80 is a molded header assembly made from a polymeric or plastic material, which may be integrated or separable from the main portion of ICM 15A.

Figure 5:
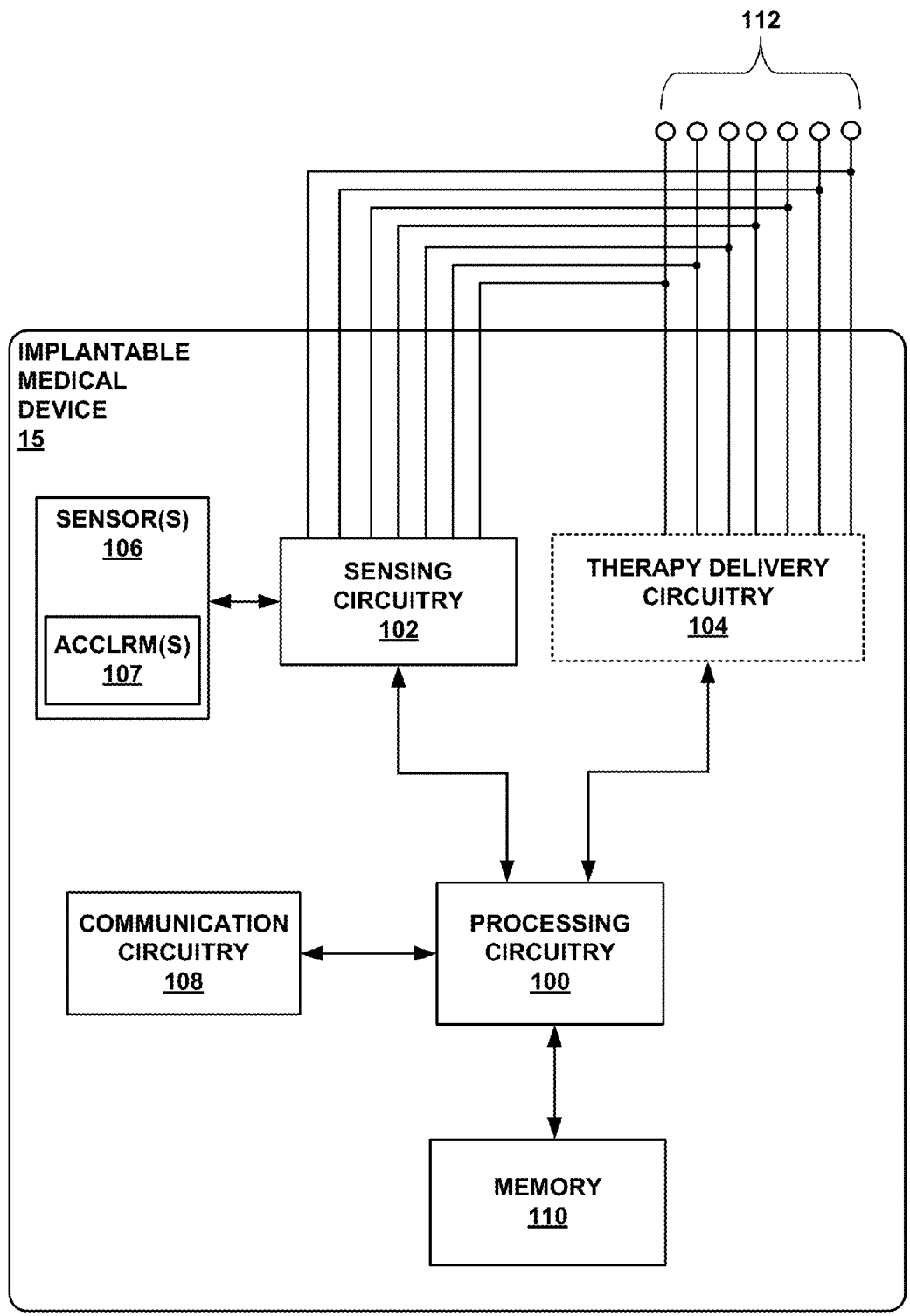
FIG. 5 is a functional block diagram illustrating an example configuration of an implantable medical device (IMD).

FIG. 5 is a functional block diagram illustrating an example configuration of an IMD 15. IMD 15 may correspond to ICM 15A in FIG. 1A and FIG. 5, IMD 15B in FIG. 1B, or another IMD configured to implement the techniques for determining whether to store or discard cardiovascular pressure measurements as described in this disclosure. In the illustrated example, IMD 15 includes processing circuitry 100 and an associated memory 110, sensing circuitry 102, therapy delivery circuitry 104, one or more sensors 106, and communication circuitry 108. However, an IMD 15 need not include all of these components, or may include additional components. For example, ICM 15A may not include therapy delivery circuitry 104, in some examples.

Memory 110 includes computer-readable instructions that, when executed by processing circuitry 100, cause IMD 15 and processing circuitry 100 to perform various functions attributed to IMD 15 and processing circuitry 100 herein. Memory 110 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processing circuitry 100 may include fixed function circuitry and/or programmable processing circuitry. Processing circuitry 100 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 100 may include multiple components, such as any combination of one or more microprocessors, one or more controllers, one or more DSPs, one or more ASICs, or one or more FPGAs, as well as other discrete or integrated logic circuitry. The functions attributed to processing circuitry 100 herein may be embodied as software, firmware, hardware or any combination thereof.

Sensing circuitry 102 and therapy delivery circuitry 104 are coupled to electrodes 112. Electrodes 112 illustrated in FIG. 6 may correspond to, for example, electrodes carried on leads 18, 20, 22 of device 15B (FIG. 1B), or electrodes 64 and 66 of ICM 15A. Sensing circuitry 102 may monitor signals from a selected two or more of electrodes 112 in order to monitor electrical activity of heart, impedance, or other electrical phenomenon. Sensing of a cardiac electrical signal may be done to determine heart rates or heart rate variability, or to detect arrhythmias (e.g., tachyarrhythmias or bradycardia) or other electrical signals. In some examples, sensing circuitry 102 may include one or more filters and amplifiers for filtering and amplifying a signal received from electrodes 112. In some examples, sensing circuitry 102 may sense or detect physiological parameters, such as heart rate, blood pressure, respiration, and the like.

The resulting cardiac electrical signal may be passed to cardiac event detection circuitry that detects a cardiac event when the cardiac electrical signal crosses a sensing threshold. The cardiac event detection circuitry may include a rectifier, filter and/or amplifier, a sense amplifier, comparator, and/or analog-to-digital converter. Sensing circuitry 102 outputs an indication to processing circuitry 100 in response to sensing of a cardiac event (e.g., detected P-waves or R-waves).

In this manner, processing circuitry 100 may receive detected cardiac event signals corresponding to the occurrence of detected R-waves and P-waves in the respective chambers of heart. Indications of detected R-waves and P-waves may be used for detecting ventricular and/or atrial tachyarrhythmia episodes, e.g., ventricular or atrial fibrillation episodes. Some detection channels may be configured to detect cardiac events, such as P- or R-waves, and provide indications of the occurrences of such events to processing circuitry 100, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

Sensing circuitry 102 may also include a switch module to select which of the available electrodes 112 (or electrode polarities) are used to sense the heart activity. In examples with several electrodes 112, processing circuitry 100 may select the electrodes that function as sense electrodes, i.e., select the sensing configuration, via the switch module within sensing circuitry 102. Sensing circuitry 102 may also pass one or more digitized EGM signals to processing circuitry 100 for analysis, e.g., for use in cardiac rhythm discrimination.

In the example of FIG. 5, IMD 15 includes one or more sensors 106 coupled to sensing circuitry 102. Although illustrated in FIG. 6 as included within IMD 15, one or more of sensors 106 may be external to IMD 15, e.g., coupled to IMD 15 via one or more leads, or configured to wirelessly communicate with IMD 15. In some examples, sensors 106 transduce a signal indicative of a patient parameter, which may be amplified, filtered, or otherwise processed by sensing circuitry 102. In such examples, processing circuitry 100 determines values of patient parameters based on the signals. In some examples, sensors 106 determine the patient parameter values, and communicate them, e.g., via a wired or wireless connection, to processing circuitry 100.

In some examples, sensors 106 include one or more accelerometers 107, e.g., one or more three-axis accelerometers. Signals generated by the one or more accelerometers 107 may be indicative of, as examples, gross body movement (e.g., activity) of the patient, patient posture, heart sounds or other vibrations or movement associated with the beating of the heart, or coughing, rales, or other respiration abnormalities. Accelerometers 107 may produce and transmit signals to processing circuit 100 for a determination as to whether the patient is in a target posture during a measurement of cardiovascular pressure by a pressure sensing device. In some examples, sensors 106 include one or more microphones configured to detect heart sounds or respiration abnormalities, and/or other sensors configured to detect patient activity or posture, such as gyroscopes and/or strain gauges. In some examples, sensors 106 may include sensors configured to transduce signals indicative of blood flow, oxygen saturation of blood, or patient temperature, and processing circuitry 100 may determine patient parameters values based on these signals. Sensors 106 may gather data that includes numerical values or waveforms of patient parameters. Data indicating the waveform may be stored in memory 110 and transmitted to another device through communication circuitry 108.

Therapy delivery circuitry 104 is configured to generate and deliver electrical therapy to the heart. Therapy delivery circuitry 104 may include one or more pulse generators, capacitors, and/or other components capable of generating and/or storing energy to deliver as pacing therapy, defibrillation therapy, cardioversion therapy, other therapy or a combination of therapies. In some instances, therapy delivery circuitry 104 may include a first set of components configured to provide pacing therapy and a second set of components configured to provide anti-tachyarrhythmia shock therapy. In other instances, therapy delivery circuitry 104 may utilize the same set of components to provide both pacing and anti-tachyarrhythmia shock therapy. In still other instances, therapy delivery circuitry 104 may share some of the pacing and shock therapy components while using other components solely for pacing or shock delivery.

Therapy delivery circuitry 104 may include charging circuitry, one or more charge storage devices, such as one or more capacitors, and switching circuitry that controls when the capacitor(s) are discharged to electrodes 112 and the widths of pulses. Charging of capacitors to a programmed pulse amplitude and discharging of the capacitors for a programmed pulse width may be performed by therapy delivery circuitry 104 according to control signals received from processing circuitry 100, which are provided by processing circuitry 100 according to parameters stored in memory 110. Processing circuitry 100 controls therapy delivery circuitry 104 to deliver the generated therapy to the heart via one or more combinations of electrodes 112, e.g., according to parameters stored in memory 110. Therapy delivery circuitry 104 may include switch circuitry to select which of the available electrodes 112 are used to deliver the therapy, e.g., as controlled by processing circuitry 100.

Communication circuitry 108 includes any suitable hardware, firmware, software or any combination thereof for communicating with another device, such as an external device 14 or another IMD or sensor. Under the control of processing circuitry 100, communication circuitry 108 may receive downlink telemetry from and send uplink telemetry to an external device 14 or another device with the aid of an antenna, which may be internal and/or external. In some examples, communication circuitry 108 may communicate with a local external device, and processing circuitry 100 may communicate with a networked computing device via the local external device and a computer network, such as the Medtronic CareLink® Network developed by Medtronic, plc, of Dublin, Ireland.

A clinician or other user may retrieve data from IMD 15 using external device 14 or another local or networked computing device configured to communicate with processing circuitry 100 via communication circuitry 108. The clinician may also program parameters of IMD 15 using external device 14 or another local or networked computing device. In some examples, the clinician may select times of day and target posture(s) for cardiovascular pressure measurements.

Communication circuitry 108 may also be configured to communicate with an implantable pressure sensing device 12. Processing circuitry 100 may receive measured cardiovascular pressure values, e.g., PAP values, from pressure sensing device 12 via communication circuitry 108. In some examples, processing circuitry 100 may send a trigger signal to sensing device 12 via communication circuitry 108 to control the sensing device to measure cardiovascular pressure in response to the trigger signal.

Although not illustrated in FIG. 5, communication circuitry 108 may be coupled or coupleable to electrodes 112 for tissue conductance communication (TCC) via the electrodes. In some examples, communication with sensor device 12 and external device 14 may be via RF telemetry or TCC. In one example, communication circuitry 108 may be configured for RF telemetry communication with external device 14 and TCC with sensor device 12.

Figure 6:
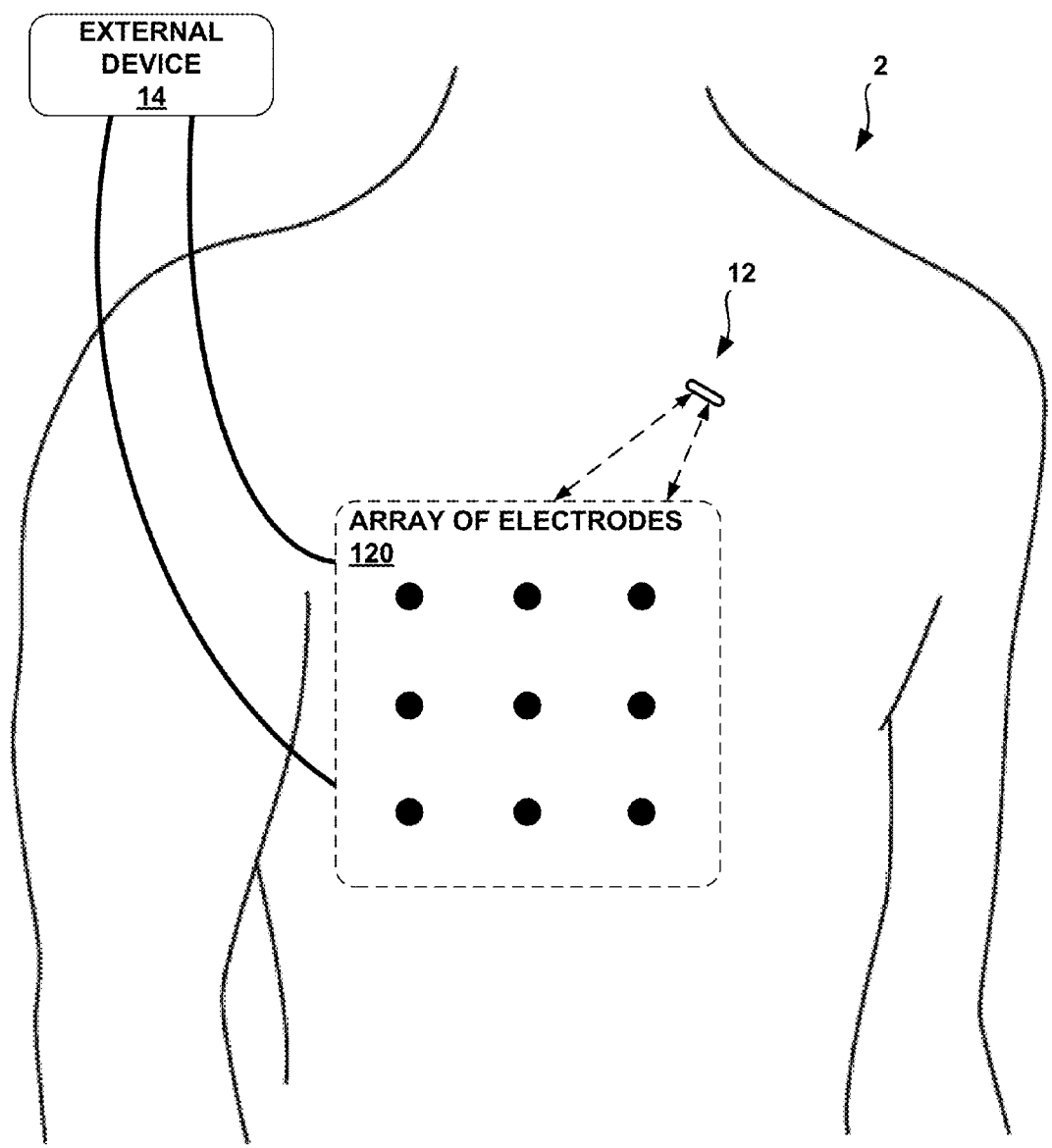
FIG. 6 is a conceptual diagram illustrating an array of electrodes positioned on a patient.

FIG. 6 is a conceptual diagram illustrating an array of electrodes 120 positioned on a patient 2. A clinician may position array of electrodes 120 on the chest or back of patient 2. Array of electrodes 120 may be connected to external device 14. The processing circuitry of external device 14 may be configured to measure the signal strength of TCC signals transmitted between a plurality of combinations or vectors of the array of electrodes 120 and sensor device 12 within patient 2. External device 14 may be configured to measure the strength of signals received from sensor device 12 by a plurality of combinations or vectors of the array of electrodes 120. In some examples, sensor device 12 may be configured to measure the strength of signals received by sensor device 12 from array of electrodes 120 and to communicate data relating to the measured signal strengths to external device 14.

External device 14 may cause combinations or vectors, also referred to as sets, of two or more electrodes of array of electrodes 120 to communicate via TCC signals with sensor device 12. In some examples, external device 14 may select pairs of electrodes in array of electrodes 120 to communicate via TCC signals with sensor device 12. Different sets of electrodes may include different electrodes and/or different polarities of one or more of the included electrodes. Based on the signal strengths for each set of one or more electrodes, external device 14 may be configured to determine a position and an orientation for another IMD to be implanted within patient 2.

In some examples, array of electrodes 120 may be configured to sense ECG signals generated by the heart of patient 2. External device 14 may cause combinations or vectors, also referred to as sets, of two or more electrodes of array of electrodes 120 to sense the ECG signals. In some examples, external device 14 may select pairs of electrodes in array of electrodes 120 to sense the ECG signals. Different sets of electrodes may include different electrodes and/or different polarities of one or more of the included electrodes. Based on the signal strengths received by each set of one or more electrodes, external device 14 may be configured to determine a position and an orientation for an IMD to be implanted within patient 2. In some examples, external device 14 may be configured to select the position and the orientation for the IMD to be implanted.

External device 14 of FIG. 6 may be the same external device as external device 14A of FIG. 1A or external device 14B of FIG. 1B. External device 14 may be a programmer for a medical device system. External device 14 may be configured to provide the functionality of being coupled to array of electrodes 120 and delivering test signals to patient 2 and the like, as described herein. In some examples, external device 14 may be a different external device that provides the functionality associated with this disclosure but may not necessarily provide the programming functionality described with respect to external devices 14A and 14B in FIGS. 1A and 1B.

Figure 7:
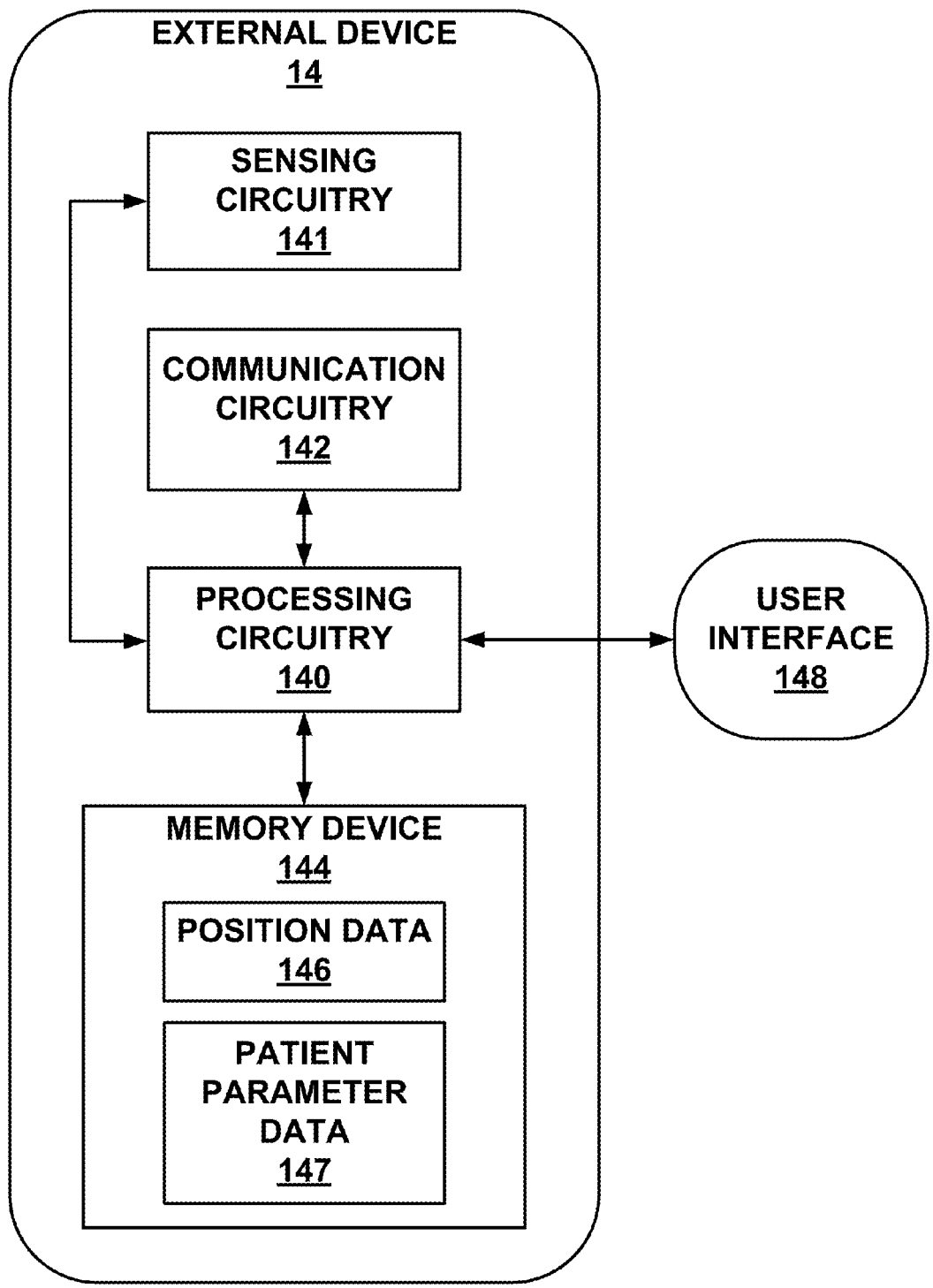
FIG. 7 is a functional block diagram illustrating an example external device configured to output to a user an indication of a position for implanting the first IMD.

FIG. 7 depicts an example external device 14, e.g., external device 14A of FIG. 1A or external device 14B of FIG. 1B, that includes processing circuitry 140 and one or more of communication circuitry 142, and memory device 144. Telemetry circuitry 142 may generate, receive, and/or test telemetry communication signals for communicating with sensor device 12 and/or IMD 15. Processing circuitry 140 may be configured to direct testing measurements to assess the suitability of an electrode for implant considering the intended therapeutic use, monitoring use and intra-device communication. Communication circuitry 142 may include signal generation circuitry configured to generate communication signals to transmit to sensing device 12, monitoring device 15A, and/or IMD 15B. Processing circuitry 140 may control switching circuitry of communication circuitry 142 for connecting to various sets of electrodes to signal transmission and receiving circuitry of communication circuitry 142 and, in some cases, to amplification, filtering and other circuitry of sensing circuitry 141 to sense an ECG. Processing circuitry 140 may be configured to control the switching circuitry based on instructions stored in memory device 144. Memory device 144 may be configured to store position data 146 and patient parameter data 147. Memory device 144 may be configured to store instructions that, when executed by processing circuitry 140, cause processing circuitry 140 to perform the techniques described herein.

Processing circuitry 140 may be configured to store in memory device 144 measurements of signals transmitted or received by communication circuitry 142. The measurements may include signal strength, signal distortion, and any other suitable parameters relating to communication signals. The measurements may also include data indicating the set of electrodes that transmitted or received the particular communication signals. In some examples, the functionality ascribed to external device 14 and processing circuitry 140 can be performed by one or more devices, in addition to or alternatively to external device 14.

In some examples, communication circuitry 142 and sensing circuitry 141 may be connected to array of electrodes 120 in FIG. 6 such that processing circuitry 140 can determine the electrodes from which a signal is transmitted or the electrodes at which a signal is received. Processing circuitry 140 may be configured to determine the set(s) of electrodes of array of electrodes 120 that produced the strongest signals and/or least distortion. In some examples, sensing circuitry 141 may be coupled to electrodes that are configured to test the sensing of ECG signals.

Processing circuitry 140 may also include localization circuitry configured to identify the position of sensor device 12 and/or IMD 15 or the electrodes of sensor device 12 and/or IMD 15 within patient 2. The localization circuitry may be configured to determine the position of a device based one or more forms of data in position data 146. Position data 146 may include an image such as a fluoroscopic image, an x-ray image, a computed tomography (CT) image, a magnetic resonance imaging (Mill) image, or an anterior-posterior image of patient 2. In some examples, position data 146 may include the position of the device entered by a clinician on a graphical representation of a human body via, for example, user interface 148. User interface 148 may be configured to display data received from display circuitry of processing circuitry 140. In some examples, user interface 148 may be a part of external device 14. External device 14 may include an integral computing device with a user interface such as a laptop computer, a tablet, and/or a smartphone. User interface 148 may also be configured to receive user input such as patient parameter data 147 and/or position data.

In some examples, a clinician may place array of electrodes 120 from FIG. 6 on patient 2. The array of electrodes 120 may be connected to communication circuitry 142, and processing circuitry 140 may be configured to measure the signal strength of TCC signals transmitted between array of electrodes 120 and the IMD within patient 2. Position data 146 may also include the strength of signals received from the device by array of electrodes 120 positioned on patient 2 or the strength of signals received by the device from array of electrodes 120 positioned on patient 2. In some examples, position data 146 may include the strength of an electrocardiogram signal received by array of electrodes 120 positioned on patient 2.

Position data 146 may indicate the location and/or orientation of a device within patient 2. The orientation of a device may include the angle at which the device is positioned within patient 2. The location and orientation of the device may also include the location and orientation of each of the electrodes in the device. For example, a device may include two electrodes that are configured to operate as a dipole. Position data 146 may include information about the locations of each of the electrodes and the angle of the dipole. Patient parameter data 147 may include the age, gender, height, weight, and chest circumference of patient 2.

Processing circuitry 140 may present information via user interface 148 for the clinician operator during a procedure using external device 14, including information regarding the telemetry communication, testing, position, or other information. Processing circuitry 140 may cause a display device of user interface 148 to display the position of a device that is implanted within patient 2. Processing circuitry 140 may be configured to cause the display device to display a recommended position for another device to be implanted within patient 2. In some examples, processing circuitry 140 may cause the display device to display a graphical representation of a human body. Processing circuitry 140 may be configured to receive user input indicating the location of the device with patient 2.

These circuits and their functions are described herein in further detail. While external device 14 of FIG. 7 is depicted comprising all four circuits in one device, external device 14 may include only a portion of the circuits and/or more include additional circuits. Moreover, external device 14 may further comprise one or more separate devices, e.g., a telemetry device, an analyzer device, a localization device, a memory device, and/or a display device. In this manner, the circuits of external device 14 may be constructed and combined in other combinations or all four could be separate.

Figure 8:
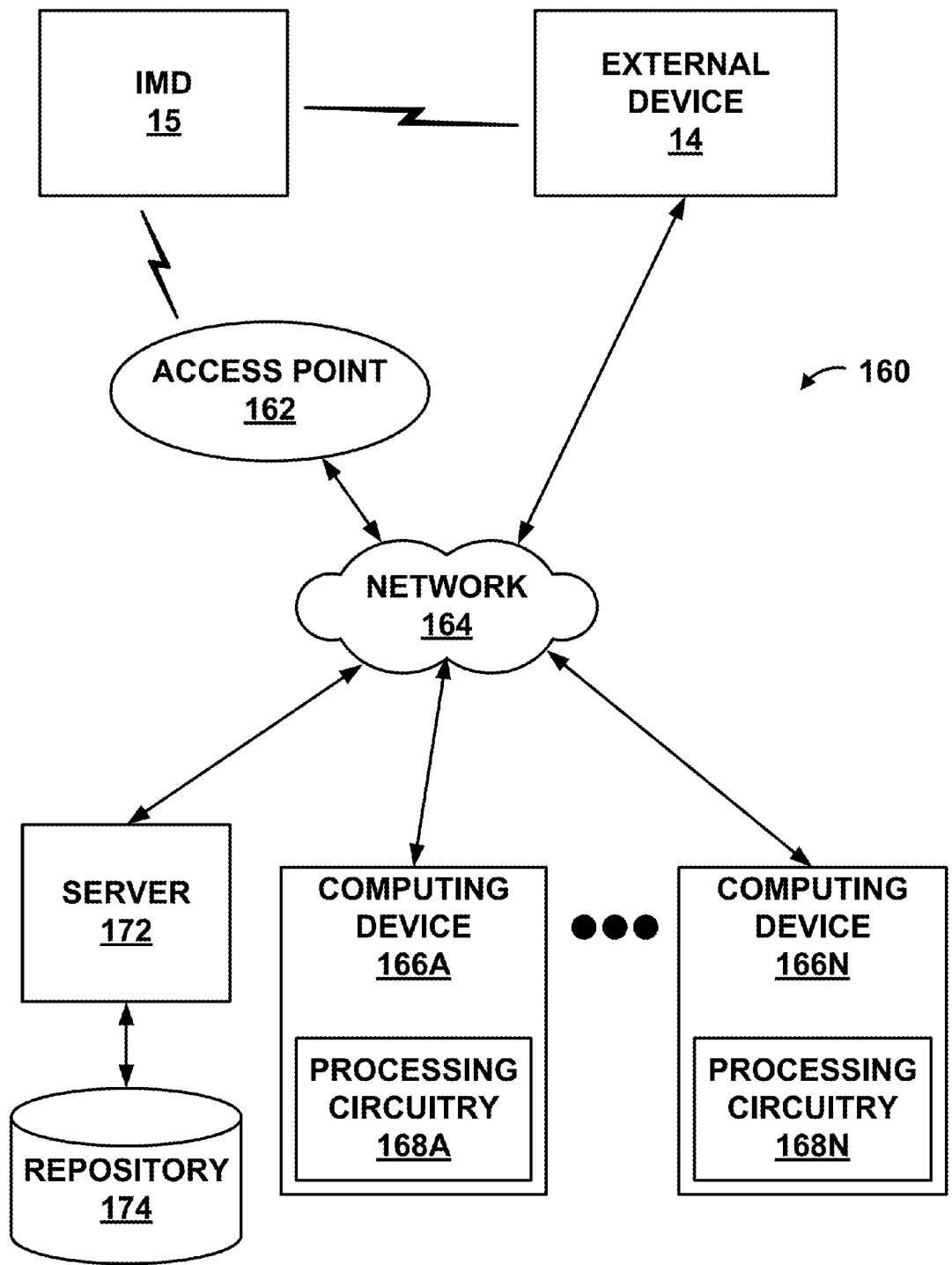
FIG. 8 is a functional block diagram illustrating an example system that includes external computing devices communicating via a network.

FIG. 8 is a functional block diagram illustrating an example system 100 that includes external computing devices, such as a server 172 and one or more other computing devices 166A-166N, that are coupled to IMD 15, sensing device 12, and external device 14 via a network 164. In this example, IMD 15 may, e.g., at different times and/or in different locations or settings, communicate with external device 14 via a first wireless connection, and to communication with an access point 162 via a second wireless connection. In the example of FIG. 8, access point 162, external device 14, server 172, and computing devices 166A-166N are interconnected, and able to communicate with each other, through network 164.

Access point 162 may comprise a device that connects to network 164 via any of a variety of connections, such as telephone dial-up, digital subscriber line (DSL), or cable modem connections. In other examples, access point 162 may be coupled to network 164 through different forms of connections, including wired or wireless connections. In some examples, access point 162 may be co-located with the patient. Access point 162 may interrogate IMD 15, e.g., periodically or in response to a command from the patient or network 164, to retrieve cardiovascular pressure measurements, corresponding times of day, corresponding posture data, and/or other operational or patient data from IMD 15. Access point 162 may provide the retrieved data to server 172 via network 164.

In some cases, server 172 may be configured to provide a secure storage site for data that has been collected from IMD 15, sensing device 12, and/or external device 14. In some cases, server 172 may assemble data in web pages or other documents for viewing by trained professionals, such as clinicians, via computing devices 166A-166N. The illustrated system of FIG. 8 may be implemented, in some aspects, with general network technology and functionality similar to that provided by the Medtronic CareLink® Network developed by Medtronic plc, of Dublin, Ireland. Server 172 may store data in repository 174, such as model data, patient parameter data, second IMD position data, and/or any other data used for identifying a position for a first IMD. Repository 174 may be configured to store an analysis module, a database, and/or lookup table that server 172 may query to retrieve data to use in identifying a position for a first IMD.

In some examples, one or more of access point 162, server 172, or computing devices 166A-166N may be configured to perform, e.g., may include processing circuitry configured to perform, some or all of the techniques described herein, e.g., with respect to processing circuitry 140 of external device 14, relating to identifying a position within patient 2 for an IMD to be implanted. Server 172 may include a memory device configured to store model data that associates patient parameter data indicating one or more anatomical or physiological parameters of patient 2, along with corresponding patient parameter data such as height, weight, chest circumference, gender, and/or age, received from a user interface and/or external device 14, which may be configured to provide some or all of the functionality ascribed to server 172 and/or computing devices 166A-166N.

For example, the processing circuitry of external device 14, or the processing circuitry of one of computing devices 166A-166N, may compare the model data to the patient parameter data and position data to determine a position for a device to be implanted. The comparison may involve querying a database of expected TCC performance based on locations and orientations of IMDs within a patient. In some examples, the processing circuitry may be configured to compare the model data in addition to or in the alternative to performing real-time computer simulations based on torso model(s) and the conductivity and permittivity of organs and tissue. The processing circuitry may output to a user an indication of the position for the device to be implanted within patient 2 based on the comparison of the model data to the patient parameter data and the position data. The processing circuitry may output the indication by causing a display device to generate a graphical representation of the device at a recommended position within a human body. The processing circuitry may cause the display device to display text indicating the recommended position to implant the device.

In some examples, a clinician may interact with a software program with a generic patient image. Using the clinician's best judgment (ascertained through medical imaging), the relative location and orientation (in three dimensions) may be approximated for the already implanted device. Generic patient demographics are selected from a pre-populated list, such as a barrel-chested male with a weight of 180 to 210 pounds. Information may be exchanged with a networked database, and one or more suggested secondary device locations/orientations may be identified. Parameters considered during the identification of the one or more positions may include just TCC performance, or TCC performance and other clinical indicators, such as R-wave amplitude or other cardiac electrogram quality parameters at specific positions and orientations for an IMD to be implanted.

Figure 9:
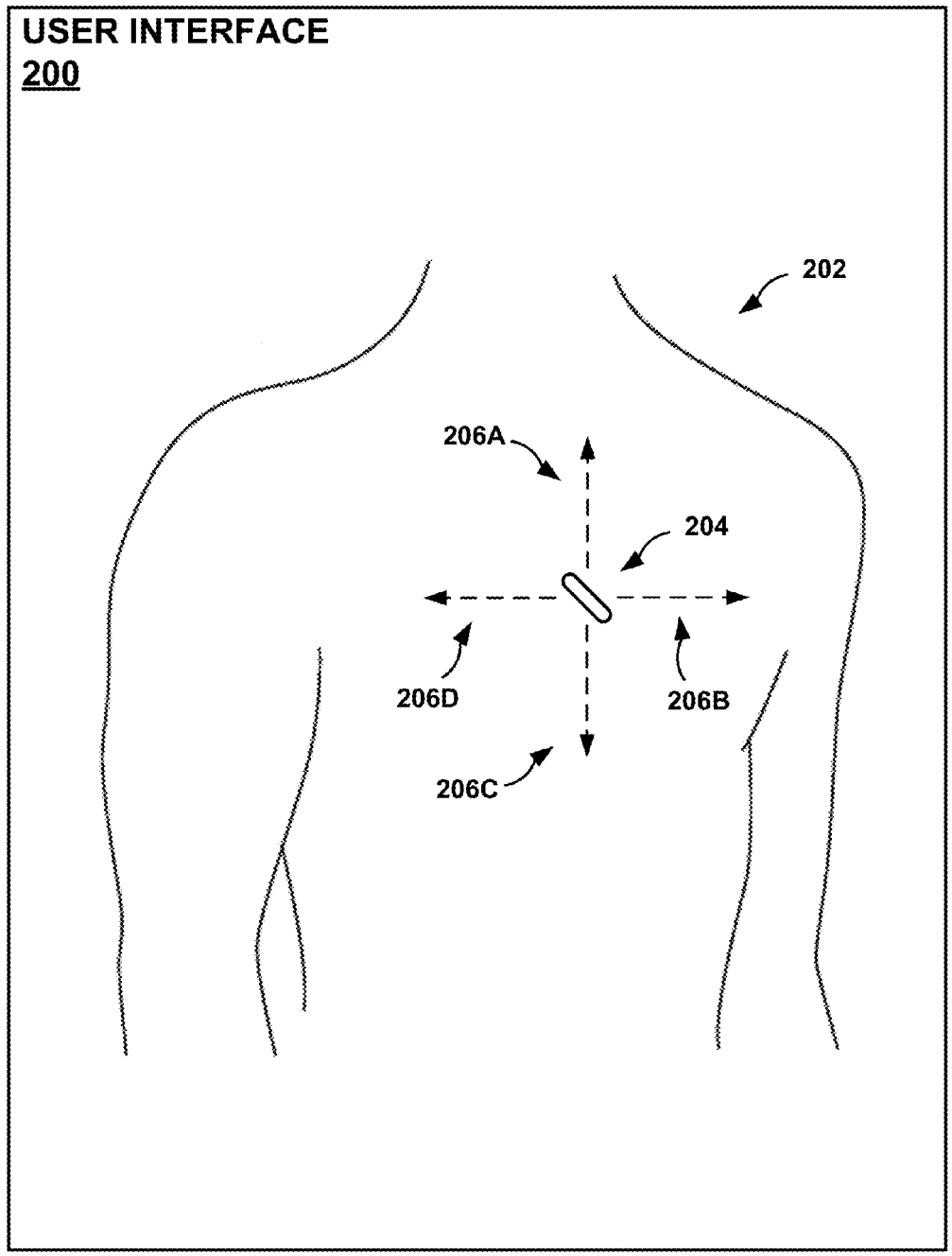
FIG. 9 illustrates a user interface including a graphical representation of a human body and configured to indicate a position for implanting the first IMD.

FIG. 9 illustrates an example user interface 200 including a graphical representation 202 of a human body and configured to indicate a position for implanting the first IMD. Graphical representation 202 may be displayed on user interface 200 on a display device, touchpad, tablet, smartphone, monitor, television, and/or any other suitable user interface. A clinician or other user may move graphical icon 204, which represents an IMD, to a position within the human body. The clinician may move graphical icon 204 up by pressing, selecting, or clicking arrow 206A, right by pressing, selecting, or clicking arrow 206B, down by pressing, selecting, or clicking arrow 206C, left by pressing, selecting, or clicking arrow 206D. In some examples, user interface 200 and graphical representation 202 may display a three-dimensional image of a human body and allow a clinician to select the position of graphical icon 204 in three dimensions.

Graphical icon 204 may represent an IMD that is already implanted with a patient. A clinician may move graphical icon 204 within graphical representation 202 to input the position of the IMD with the patient. The clinician may first review a fluoroscopic image and/or an anterior-posterior image before selecting a position for graphical icon 204. The clinician may select the position for graphical icon 204 based on the position of the IMD displayed with the fluoroscopic image and/or anterior-posterior image. The clinician may provide input data by entering or selecting a position for graphical icon 204 on graphical representation 202.

In some examples, graphical icon 204, or an additional graphical icon (not shown in FIG. 9), may represent a proposed position for an IMD that has not yet been implanted. User interface 200 may allow a clinician to select a position for graphical icon 204 within graphical representation 202. User interface 200 may then display operating characteristics of the selected position for graphical icon 204, where the operating characteristics may include TCC communication performance. The operating characteristics may also include the performance of detecting sensing signals and/or delivering therapy pulses. The clinician may use the displayed operating characteristics to evaluate the selected position as a possible position for the IMD to be implanted with the patient.

Figure 10:
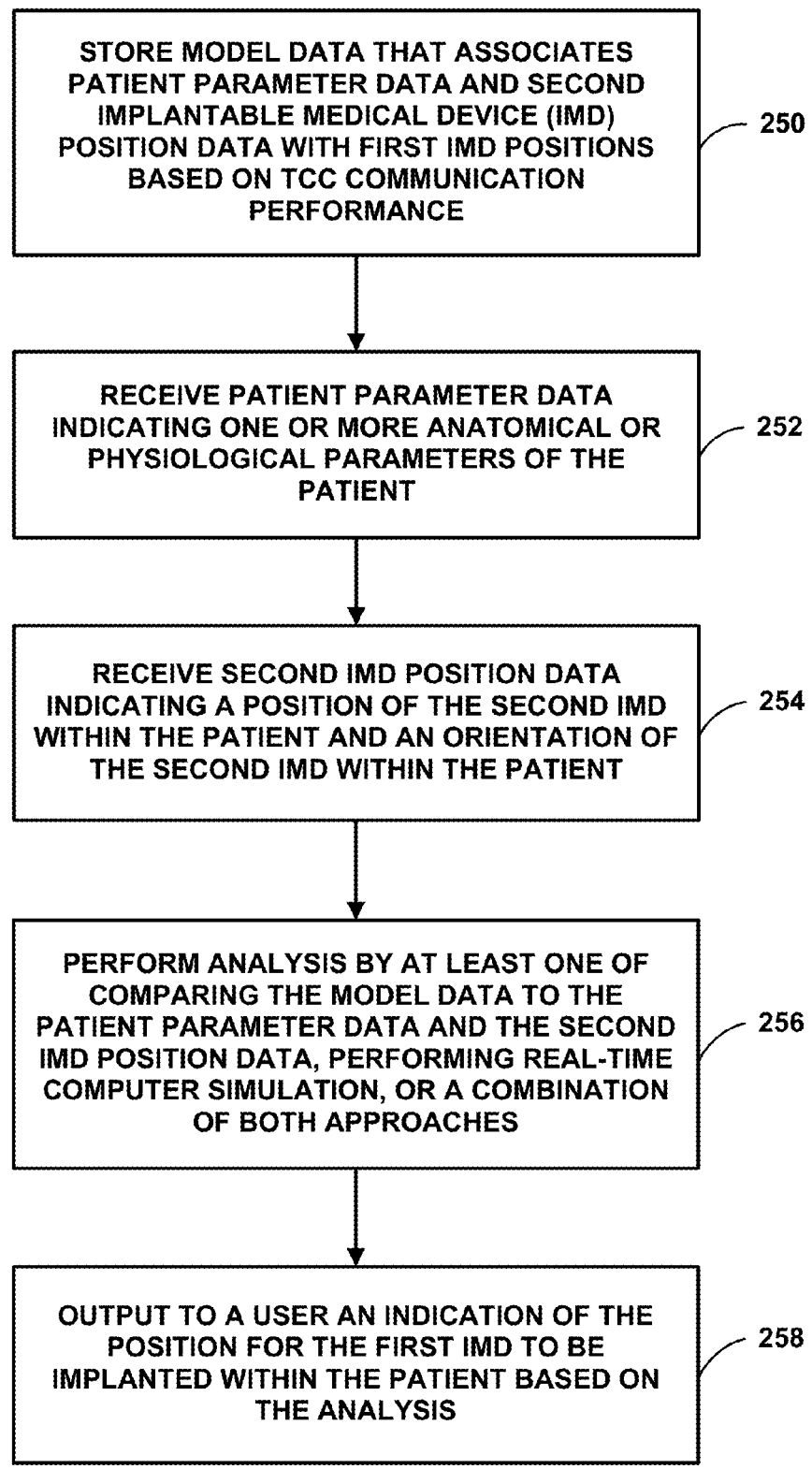
FIG. 10 is a flowchart illustrating an example technique for indicating a position for implanting the first IMD that may be implemented by a computing device, in accordance with this disclosure.

FIG. 10 is a flowchart illustrating an example technique for indicating a position for implanting the first IMD that may be implemented by a computer device such as external device 14, one or more of computing devices 166A-166N, and/or server 172 in accordance with this disclosure. Processing circuitry 140 of external device 14, one or more of computing devices 166A-166N, server 172, and/or another device of this disclosure may perform the techniques of FIG. 10.

According to the example of FIG. 10, processing circuitry 140 of external device 14 may be configured to store model data that associates patient parameter data and second IMD position data with first IMD positions based on TCC communication performance in memory device 144 (250). In some examples, the model data may include vectors representing the propagation of TCC signals through body tissue. The model data may also include data representing the permittivity and/or conductivity of various types of body tissue. The model data may include a representation of a human body and locations of the various types of body tissue within the human body.

Processing circuitry 140 may be further configured to receive patient parameter data indicating one or more anatomical or physiological parameters of the patient (252). The patient parameter data may include height, weight, chest circumference, age, gender, and/or any other patient parameters. A clinician or the patient may input the patient parameter data via user interface, such as a computer or tablet. In some examples, the processing circuitry may obtain the patient parameter data from medical records.

Processing circuitry 140 may be further configured to receive second IMD position data indicating a position of the second IMD within the patient and an orientation of the second IMD within the patient (254). The second IMD position data may include a fluoroscopic image, x-ray image, CT image, and/or an anterior-posterior image of the second IMD within the patient. The second IMD position data may include signal strength data for signals transmitted between an array of electrodes position on the patient's body and the second IMD. The second IMD may be any IMD, such as sensing device 12, monitoring device 15A, or IMD 15B.

Processing circuitry 140 may be further configured to perform analysis by at least one of comparing the model data to the patient parameter data and the second IMD position data, performing real-time computer simulations, or a combination of both approaches (256). The model data may include an analysis module, a database, and/or lookup table that associates each possible position and patient parameter data with electromagnetic characteristics for TCC performance. The processing circuitry may be configured to compare by at least modifying the geometry of the patient model based on patient parameter data, such that the size or electromagnetic characteristics of the patient model may change based on the patient parameters.

The processing circuitry of external device 14 may be further configured to output to a user an indication of the position for the first IMD to be implanted within the patient based on the analysis (258). The indication may be output to a display device to show or explain to the user the recommended position for the first IMD. The indication may also include a recommended location on the patient to insert the first IMD. The indication may depict or explain the location in relation to the structures of the patient's body, including bones, organs, tissue, etc. The recommended position for the first IMD may be a position at which the TCC signal strength between the first IMD and the second IMD may be higher than other possible implant positions.

Figure 11:
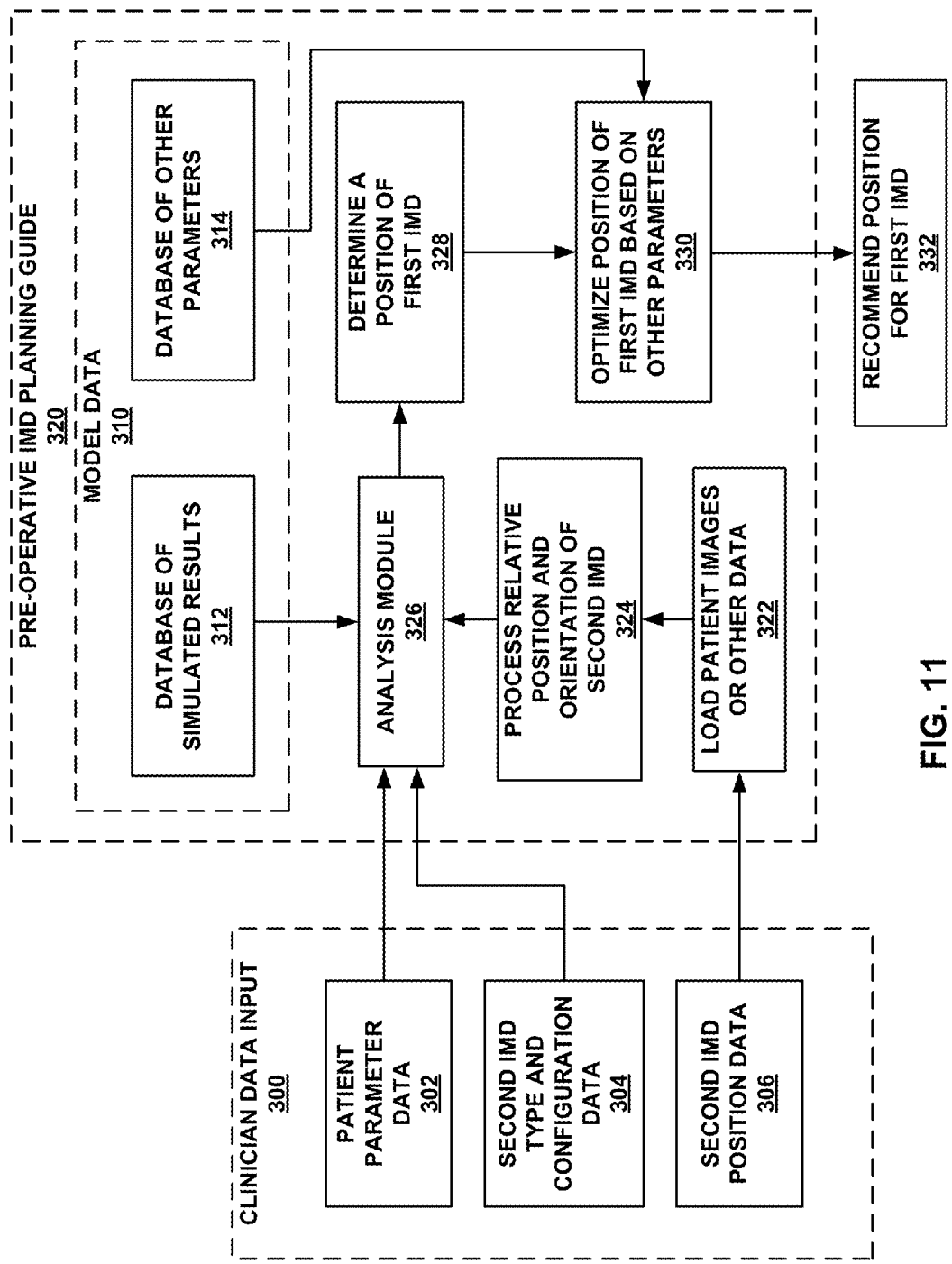
FIG. 11 is a flowchart illustrating another example technique for indicating a position for implanting the first IMD that may be implemented by a computing device, in accordance with this disclosure.

FIG. 11 is a flowchart illustrating another example technique for indicating a position for implanting the first IMD that may be implemented by a computing device, in accordance with this disclosure. According to the example of FIG. 11, the processing circuitry of the computing device may implement pre-operative IMD planning guide 320 and may be configured to receive clinician input data 300, which may include patient parameter data 302, second IMD type and configuration data 304, and second IMD position data 306. Second IMD type and configuration data 304 may include data relating to the size, shape, and positions of the electrodes of the second IMD. The clinician may load patient images of other data that includes second IMD position data 306 (322). Pre-operative IMD planning guide 320 may be configured to process the relative position and orientation of the second IMD from the patient images and other data (324).

Pre-operative IMD planning guide 320 implemented by the processing circuitry of the computing device may be configured to apply the relative position and orientation of the second IMD, patient parameter data 302, and second IMD type and configuration data 304 to an analysis module (326). The analysis module may perform real time computer simulations, perform analysis through an analysis module and/or a look up database, or use a combination of both methods. The analysis module and/or look up database may include a lookup table, a data warehouse, or a database of simulated results 312 that matches patient parameter data, second IMD positions, and first IMD positions in order to achieve desirable TCC performance characteristics. Database of simulated results 312 may include results from simulations of two IMD communicating via TCC through body tissue. Pre-operative IMD planning guide 320 may be configured to determine a position of the first IMD based on the results from the analysis module (328). In some examples, pre-operative IMD planning guide 320 may be configured to determine more than one position for the first IMD, rank the determined positions, and output the ranked positions.

Pre-operative IMD planning guide 320 may be configured to determine a position of the first IMD further based on the results from array of electrodes 120 of FIG. 6. A clinician may position array of electrodes 120 on a patient at a predetermined position. For example, array of electrodes 120 may include marking(s) for lining up the array with the sternum, spinal cord, and/or any other bones or part of the patient's body. The clinician may enter the position of array of electrodes 120 via a user interface, and processing circuitry 140 of external device 14. Processing circuitry 140 of external device 14 may be configured to determine the position of the second IMD by analyzing the signal strength of signals transmitted and received by array of electrodes 120, in addition to the other sources of second IMD position data described herein. Processing circuitry 140 may also be configured to test the sensing of physiological signals (e.g., heart rate and respiration), as well as the delivery of therapeutic signals by using sets of electrodes on array of electrodes 120.

Pre-operative IMD planning guide 320 may be configured to select, e.g., optimize, the position of the first IMD based on other parameters from database 314 (330). The other parameters may relate to the operation of the first IMD within the patient based on positioning and orientation of the second IMD. The other parameters may include the anticipated ambulatory position of the patient during targeted communication times. For example, a targeted communication time may be when the patient is sleeping. If the patient is known to favor sleeping on a particular side, that information could be another parameter that affects how pre-operative IMD planning guide 320 selects the position of the first IMD. The model data may include anticipated tissue movement in a favored sleep position, and pre-operative IMD planning guide 320 may output a position of the first IMD based on the favored sleep position. For example, two IMDs may communicate every few heart beats to coordinate pacing signals delivered to the heart. As another example, a device may measure a physiological parameter at night and communicate the measurements to another device. In some examples, an extravascular IMD may be configured to detect arrhythmia and, after detecting a possible arrhythmia, to communicate with another IMD to confirm the existence of the arrhythmia. The determination of a position and orientation for the first IMD may be based on the anticipated communication protocol between the two or more IMDs.

In some examples, if the first IMD is designed to measure heart rate and respiration, pre-operative IMD planning guide 320 may determine the expected performance in measuring heart rate and respiration of the first IMD at the recommended position. Finally, pre-operative IMD planning guide 320 may be configured to recommend a position for the first IMD within the patient (332). Pre-operative IMD planning guide 320 may be configured to output the recommended position (or ranked positions) for the first IMD to a user interface such as a display device.

A clinician such as a physician, nurse, or technician may select a position and orientation for the first IMD based on the recommended position(s) and orientation(s) from pre-operative IMD planning guide 320. Pre-operative IMD planning guide 320 may recommend positions and orientation based on TCC performance between the first IMD and the second IMD. Pre-operative IMD planning guide 320 may determine the recommendations on a backend database including model data 310 and populated with modeling results of various size patients and implant orientations. Given the input data entered by the clinician, the database will be queried for the best possible match and results will be provided to the clinician that will provide the most reliable communication between IMDs.

Pre-operative IMD planning guide 320 may be an application that can be used on a tablet or computer. The processing circuitry of external device 14 may be configured to execute instructions to perform the functions of pre-operative IMD planning guide 320. Pre-operative IMD planning guide 320 may use current information known about an implant position and orientation of an IMD within a patient, along with patient anatomic features such as height, weight, and chest circumference. Pre-operative IMD planning guide 320 may use the information to reference a back-end database of extensive simulations that may aid in identification of an optimal implant location for the first IMD.

Pre-operative IMD planning guide 320 may provide a path forward for selecting the positions of IMD to facilitate and improve the communication between multiple small IMDs such as a pressure sensor and/or an implantable loop recorder. Under normal implant conditions, there may be a non-negligible probability that communication between implants may not be reliable. Given prior information from position and orientation of one IMD, an optimal position and orientation of another IMD may be identified to significantly improve communication reliability between the two IMDs.

In some examples, pre-operative IMD planning guide 320 may be configured to perform a real-time calculation to generate a recommended position for a first IMD. The real-time calculation may be patient-specific and based on patient parameter data, position data, and model data. Alternative or additionally, pre-operative IMD planning guide 320 may be configured to transmit a query to a database via a network connection. The query may include the patient parameter data and the IMD position data. A computing device may execute the query at the database by applying model data to the patient parameter data and the IMD position data. The computing device may transmit the results from the executed query to a user device such as a mobile device or a computing device in the office of the clinician.

The flowcharts of FIGS. 10 and 11 are intended to illustrate the functional operation of external device 14, medical device system 8, computing devices 166A-166N, server 172, and other devices and systems described herein, and should not be construed as reflective of a specific form of software or hardware necessary to practice the methods described.

Figure 12:
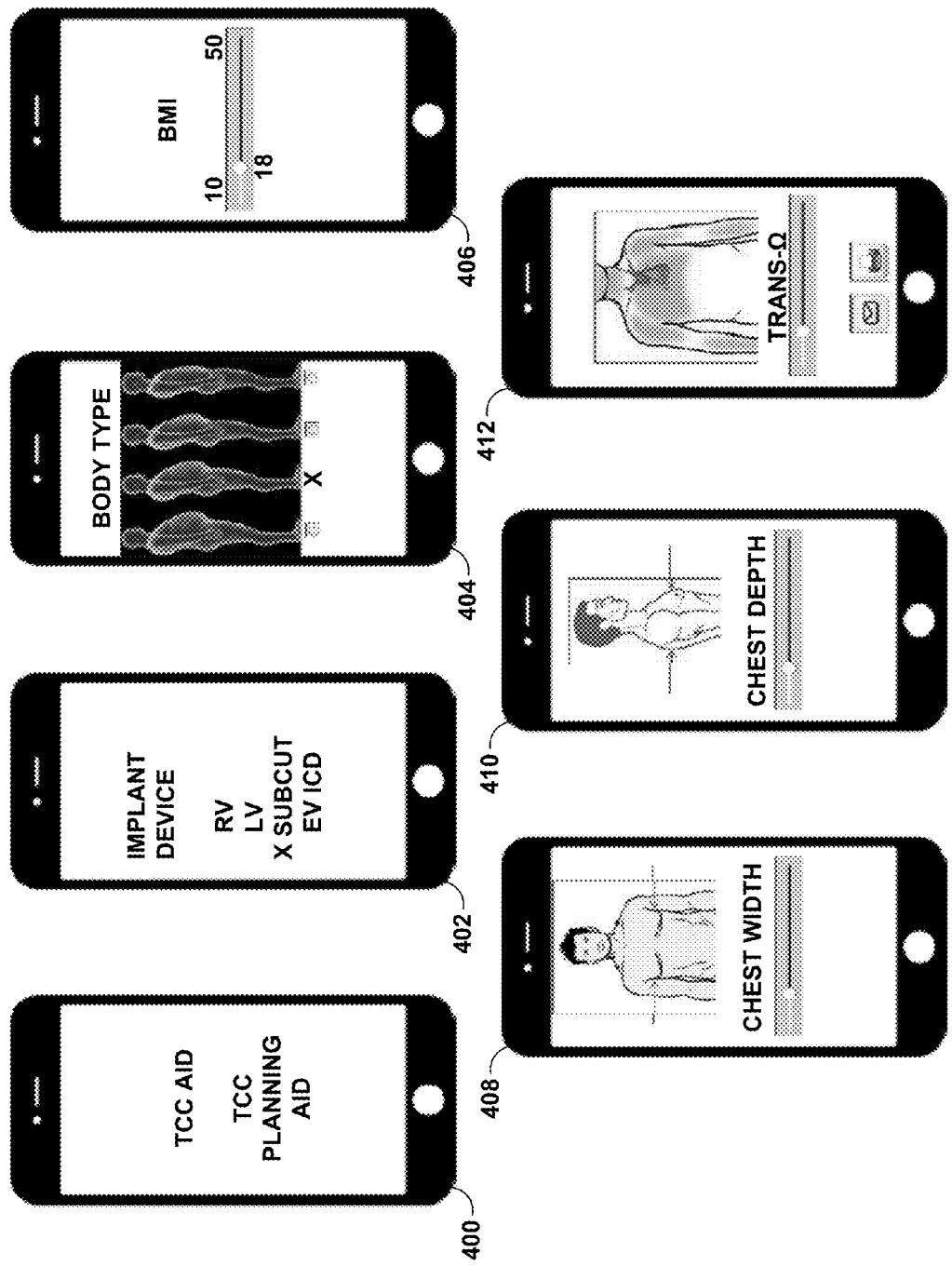
FIG. 12 illustrates example graphical user interfaces, in accordance with this disclosure.

FIG. 12 illustrates example graphical user interfaces 400-412, in accordance with this disclosure. FIG. 12 depicts a mobile device displaying user interfaces 400-412. The mobile device may be a mobile phone, a tablet, a laptop computer. In some examples, a computer monitor or any computing or display device may be configured to display user interfaces 400-412.

Using user interfaces 400-412, a clinician or other surgeon may input information regarding a type or model of IMD, a desired implant location generally, and information about the patient's body or other patient parameters. Based on this information, processing circuitry may be configured to perform analysis by at least one of comparing the model data to the patient parameter data and position data and/or performing computer simulations. Based on the analysis, the processing circuitry may select one or more implant positions for the IMD, and suggest the selected implant location(s) to the user, e.g., via a user interface. The collected information illustrated by user interfaces 400-412 is one example, and other examples may include more, less, or otherwise different information collected for purposes of determining an implant position for an IMD.

User interface 400 is an example title screen for pre-operative IMD planning guide 320. User interface 402 may be configured to allow a user to select the type of implant device and associated location, such as right ventricle (RV) implant location, left ventricle (LV) implant location, subcutaneous implant location, or an implant location for an extravascular (EV) ICD. User interface 402 may show a subcutaneous implant location being selected by the user. User interface 404 shows an example of body type selection interface with four options, although more or fewer options may be available. User interface 406 shows an example of body mass index (BMI) selection using a scrollbar. User interfaces 408 and 410 show examples of chest width selection and chest depth using scrollbars. User interface 412 shows an example of transimpedance selection using a scrollbar.

Body type, BMI, and transimpedance are examples of patient parameter data that may be collected via user interfaces to facilitate determination of an implant position for an IMD. A clinician may determine or estimate values for such parameters, e.g., based on a physical examination of the patient or patient records. Other example patient parameters include gender, age, body mass index, chest width, chest circumference, and so on.

Figure 13:
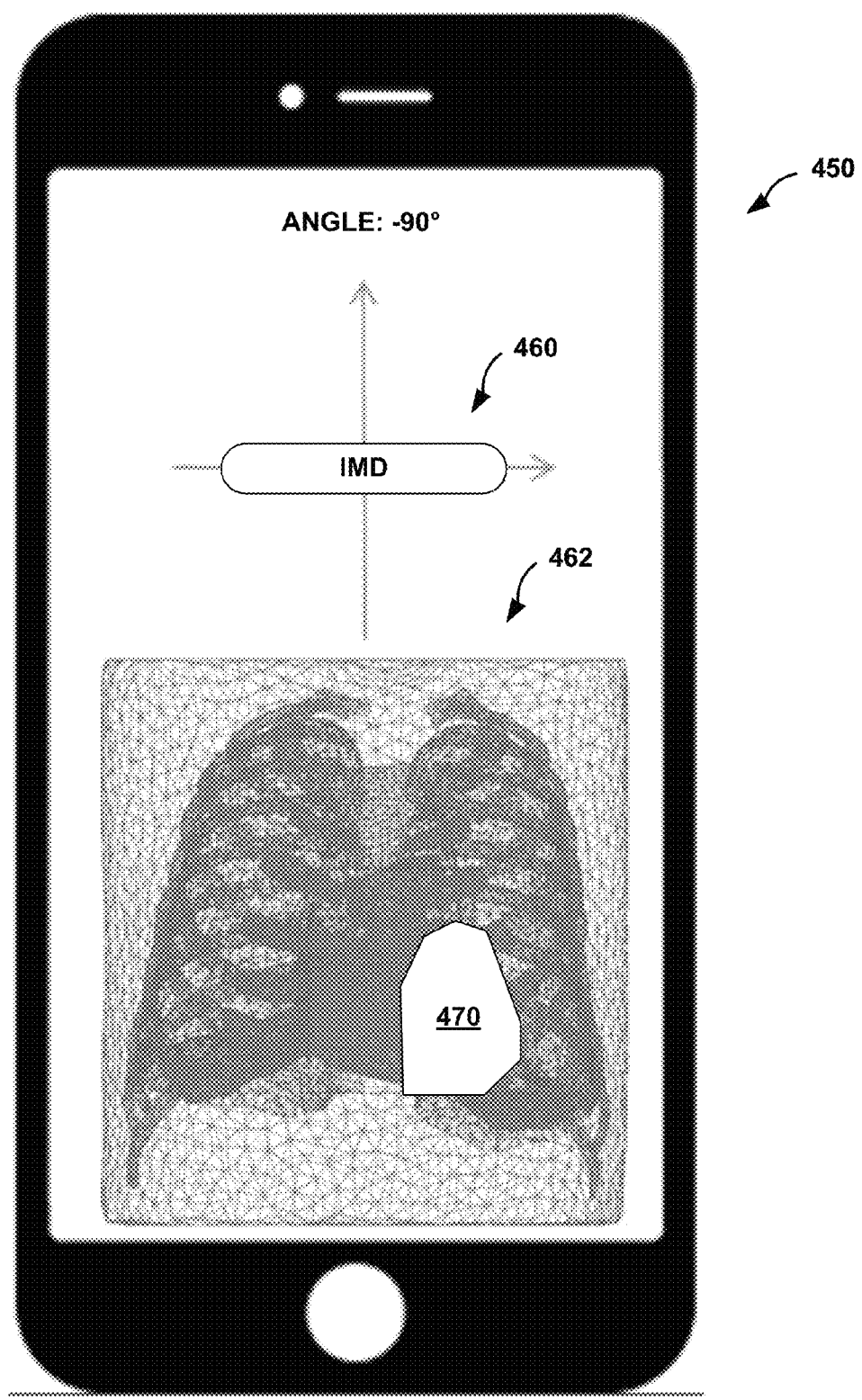
FIG. 13 illustrates an example graphical user interface including a recommended implant position, in accordance with this disclosure.

FIG. 13 illustrates an example graphical user interface 450 including a recommended implant position 470, in accordance with this disclosure. User interface 450 shows an orientation for a graphical representation of IMD 460. In the illustrated example, the orientation includes an angle of the longitudinal axis of the IMD of ninety degrees relative to a vertical orientation, e.g., a cranial-caudal orientation. Graphical representation 462 includes a model of a ribcage and thorax. The position and size of region 470 relative the ribcage and thorax may show a clinician a recommended location within a patient to implant an IMD. In this manner, user interface 450, e.g., graphical representation of IMD 460 and region 470, may illustrate a recommended position, e.g., location and orientation, for implanting an IMD.

Figure 14:
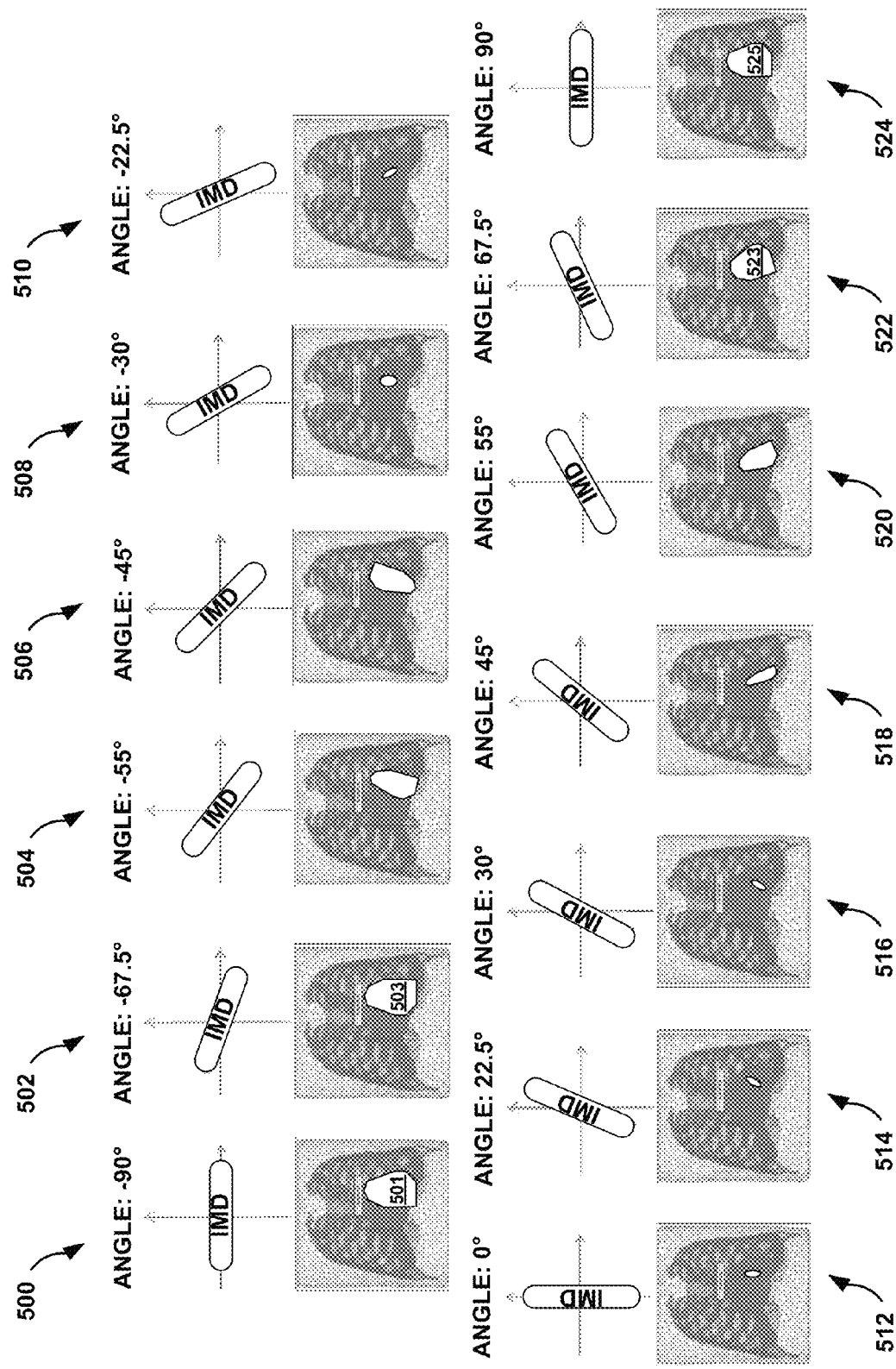
FIG. 14 illustrates example graphical user interfaces including recommended implant positions, in accordance with this disclosure.

FIG. 14 illustrates example graphical user interfaces 500-524 including possible or recommended implant positions, in accordance with this disclosure. Each of user interfaces 500-524 include a possible orientation for an IMD that includes an angle of the IMD, e.g., the IMD longitudinal axis, relative to a vertical orientation, e.g., a cranial-caudal orientation. User interfaces 500, 502, 504, 506, 518, 520, 522, and 524 include associated graphical representations of regions (e.g., regions 501, 503, 523, and 525) for recommended positions of an IMD in relation to the ribcage of a patient. User interfaces 508, 510, 512, 514, and 516 may include graphical representations of discrete recommended positions of an IMD in relation to the ribcage and thorax of a patient.

User interfaces 450 and 500-524 may assist a clinician in preparing to implant an IMD by presenting recommended orientations and positions for implantation. A user interface may include a recommended region in relation to the patient's ribcage. The dimensions of the region may show the clinician the tolerance for implantation: a larger region may mean that the IMD may operate properly in a wider range of positions, as compared to a smaller region.

In some examples, pre-operative IMD planning guide 320 may be configured to perform a real-time calculation using patient parameter data (see FIG. 12), IMD position data, and model data. Pre-operative IMD planning guide 320 may be configured to perform a real-time calculation and output the recommended orientation(s) and position(s) to the user via a graphical user interface (see FIGS. 13 and 14).

In some examples, user interface 450 (FIG. 13) may allow a user to manipulate one or both of the orientation of the graphical representation of IMD 460 or region 470. In some examples, when orientation is manipulated, user interface 450 may correspondingly change the location or region, e.g., according to the relationships between orientations and locations illustrated by user interfaces 500-524 (FIG. 14). In this manner, the user may visualize what effects changing orientation would have on location, or receive guidance regarding possible implant locations for a particular, e.g., user-preferred, orientation.

Methods described in conjunction with flow diagrams presented herein may be implemented in a non-transitory computer-readable medium that includes instructions for causing a programmable processor to carry out the methods described. A non-transitory computer-readable medium includes but is not limited to any volatile or non-volatile media, such as a RAM, ROM, CD-ROM, NVRAM, EEPROM, flash memory, or other computer-readable media, with the sole exception being a transitory, propagating signal. The instructions may be implemented by processing circuitry hardware as execution of one or more software modules, which may be executed by themselves or in combination with other software.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

The following numbered examples demonstrate one or more aspects of the disclosure.

Example 1

A method is for identifying a position within a patient for a first implantable medical device (IMD) to be implanted to facilitate tissue conductive communication (TCC) between the first IMD and a second IMD implanted within the patient. The method includes storing model data that associates patient parameter data and second IMD position data with first IMD positions based on TCC communication performance. The method further includes receiving patient parameter data indicating one or more anatomical or physiological parameters of the patient and receiving second IMD position data indicating a position of the second IMD within the patient and an orientation of the second IMD within the patient. The method also includes performing analysis by at least one of comparing the model data to the patient parameter data and the second IMD position data, performing real-time computer simulations, or using a combination of comparing the model data to the patient parameter data and the second IMD position data or performing the real-time computer simulations. The method includes outputting to a user an indication of the position for the first IMD to be implanted within the patient based on the analysis.

Example 2

The method of example 1, wherein the patient parameter data includes at least one of a height of the patient or a weight of the patient.

Example 3

The method of examples 1-2 or any combination thereof, wherein the patient parameter data includes a chest circumference of the patient.

Example 4

The method of examples 1-3 or any combination thereof, wherein the patient parameter data includes at least one of a gender of the patient or an age of the patient.

Example 5

The method of examples 1-4 or any combination thereof, wherein receiving the second IMD position data includes receiving an image of the second IMD within the patient and determining the position of the second IMD within the patient based on the image of the patient.

Example 6

The method of examples 1-5 or any combination thereof, wherein outputting the indication includes outputting to the user the indication based on the analysis and further based on a strength of a signal received from the second IMD by an array of electrodes positioned on the patient.

Example 7

The method of examples 1-6 or any combination thereof, wherein outputting the indication includes outputting to the user the indication based on the analysis and further based on a strength of a signal received by the second IMD from an array of electrodes positioned on the patient.

Example 8

The method of examples 1-7 or any combination thereof, further including determining the position for the first IMD to be implanted with the patient based on a type of the first IMD and a configuration of the first IMD, wherein outputting the indication is further based on determining the position for the first IMD.

Example 9

The method of examples 1-8 or any combination thereof, wherein the model data includes a database associating IMD locations, patient parameter data, and TCC communication performance.

Example 10

The method of examples 1-9 or any combination thereof, wherein receiving the second IMD position data includes receiving input data from a clinician, wherein the input data includes the position of the second IMD entered on a graphical representation of a human body.

Example 11

The method of examples 1-10 or any combination thereof, wherein outputting the indication includes outputting to the user the indication based on the analysis and further based on a strength of an electrocardiogram signal received by an array of electrodes positioned on the patient.

Example 12

The method of examples 1-11 or any combination thereof, wherein outputting the indication includes generating a graphical representation of at least part of a body and generating, based on the position for the first IMD, a graphical representation of a region for the first IMD. Outputting the indication further includes causing a display device to display the graphical representation of the region for the first IMD in relation to the graphical representation of the at least part of the body.

Example 13

A method is for identifying a position within a patient for a first implantable medical device (IMD) to be implanted to facilitate tissue conductive communication (TCC) between the first IMD and a second IMD implanted within the patient. The method includes receiving an image of the second IMD within the patient. The method further includes determining a position of the second IMD within the patient and an orientation of the second IMD within the patient based on the image and storing model data that associates patient parameter data and second IMD position data with first IMD positions based on TCC communication performance. The method also includes receiving patient parameter data indicating one or more anatomical or physiological parameters of the patient and performing analysis by at least one of comparing the model data to the patient parameter data and the second IMD position data, performing real-time computer simulations, or using a combination of comparing the model data to the patient parameter data and the second IMD position data or performing the real-time computer simulations. The method further includes outputting to a user an indication of the position for the first IMD to be implanted within the patient based on the analysis.

Example 14

The method of example 13, wherein the patient parameter data includes at least one of a height of the patient or a weight of the patient.

Example 15

The method of examples 13-14 or any combination thereof, wherein the patient parameter data includes a chest circumference of the patient.

Example 16

The method of examples 13-15 or any combination thereof, wherein the patient parameter data includes at least one of a gender of the patient or an age of the patient.

Example 17

The method of examples 13-16 or any combination thereof, wherein outputting the indication includes outputting to the user the indication based on the analysis and further based on a strength of a signal received from the second IMD by an array of electrodes positioned on the patient.

Example 18

The method of examples 13-17 or any combination thereof, wherein outputting the indication includes outputting to the user the indication based on the analysis and further based on a strength of a signal received by the second IMD from an array of electrodes positioned on the patient.

Example 19

The method of examples 13-18 or any combination thereof, further including determining the position for the first IMD based on a type of the first IMD and a configuration of the first IMD, wherein outputting the indication is further based on determining the position for the first IMD.

Example 20

The method of examples 13-19 or any combination thereof, wherein the model data includes a database associating IMD locations, patient parameter data, and TCC communication performance.

Example 21

The method of examples 13-20 or any combination thereof, wherein outputting the indication includes outputting to the user the indication based on the analysis and further based on a quantitative measurement of an electrocardiogram signal received by an array of electrodes positioned on the patient.

Example 22

The method of examples 13-21 or any combination thereof, wherein outputting the indication includes generating a graphical representation of at least part of a body and generating, based on the position for the first IMD, a graphical representation of a region for the first IMD. Outputting the indication also includes causing a display device to display the graphical representation of the region for the first IMD in relation to the graphical representation of the at least part of the body.

Example 23

A medical device system is for identifying a position within a patient for a first implantable medical device (IMD) to be implanted to facilitate tissue conductive communication (TCC) between the first IMD and a second IMD implanted within the patient. The medical device system includes a user interface and processing circuitry configured to store model data that associates patient parameter data and second IMD position data with first IMD positions based on TCC communication performance. The processing circuitry is further configured to receive patient parameter data indicating one or more anatomical or physiological parameters of the patient and receive second IMD position data indicating a position of the second IMD within the patient and an orientation of the second IMD within the patient. The processing circuitry is also configured to perform analysis by at least one of comparing the model data to the patient parameter data and the second IMD position data, performing real-time computer simulations, or using a combination of comparing the model data to the patient parameter data and the second IMD position data or performing the real-time computer simulations. The processing circuitry is further configured to output, via the user interface, an indication of the position for the first IMD to be implanted within the patient based on the analysis.

Example 24

The medical device system of example 23, wherein the processing circuitry is configured to receive the patient parameter data including at least one of a height of the patient or a weight of the patient.

Example 25

The medical device system of examples 23-24 or any combination thereof, wherein the processing circuitry is configured to receive the patient parameter data including a chest circumference of the patient.

Example 26

The medical device system of examples 23-25 or any combination thereof, wherein the processing circuitry is configured to receive the patient parameter data including at least one of a gender of the patient or an age of the patient.

Example 27

The medical device system of examples 23-26 or any combination thereof, wherein the processing circuitry is configured to receive the second IMD position data including an image of the second IMD within the patient and determine the position of the second IMD within the patient based on the image of the patient.

Example 28

The medical device system of examples 23-27 or any combination thereof, wherein the processing circuitry is configured to output to the user the indication based on the analysis and further based on a strength of a signal received from the second IMD by an array of electrodes positioned on the patient.

Example 29

The medical device system of examples 23-28 or any combination thereof, wherein the processing circuitry is configured to output to the user the indication based on the analysis and further based on a strength of a signal received by the second IMD from an array of electrodes positioned on the patient.

Example 30

The medical device system of examples 23-29 or any combination thereof, wherein the processing circuitry is configured to determine the position for the first IMD to be implanted with the patient based on a type of the first IMD and a configuration of the first IMD. The processing circuitry is also configured to output to the user the indication based on the analysis and further based on determining the position for the first IMD based on a type of the first IMD and a configuration of the first IMD.

Example 31

The medical device system of examples 23-30 or any combination thereof, wherein the processing circuitry is configured to store model data including a database associating IMD locations, patient parameter data, and TCC communication performance.

Example 32

The medical device system of examples 23-31 or any combination thereof, wherein the processing circuitry is configured to receive the second IMD position including input data from a clinician, wherein the input data includes the position of the second IMD entered on a graphical representation of a human body displayed on the user interface.

Example 33

The medical device system of examples 23-32 or any combination thereof, wherein the processing circuitry is configured to output to the user the indication based on the analysis and further based on a strength of an electrocardiogram signal received by an array of electrodes positioned on the patient.

Example 34

The medical device system of examples 23-33 or any combination thereof, wherein the processing circuitry is further configured to generate a graphical representation of at least part of a body and generate, based on the position for the first IMD, a graphical representation of a region for the first IMD. The processing circuitry is configured to output the indication includes causing the user interface to display the graphical representation of the region for the first IMD in relation to the graphical representation of the at least part of the body.

Example 35

A computer-readable medium includes instructions for causing at least one programmable processor of a computing device to identify a position within a patient for a first implantable medical device (IMD) to be implanted to facilitate tissue conductive communication (TCC) between the first IMD and a second IMD implanted within the patient by at least storing model data that associates patient parameter data and second IMD position data with first IMD positions based on TCC communication performance; receiving patient parameter data indicating one or more anatomical or physiological parameters of a patient; receiving second IMD position data indicating a position of a second IMD within the patient and an orientation of the second IMD within the patient; performing analysis by at least one of comparing the model data to the patient parameter data and the second IMD position data, performing real-time computer simulations, or using a combination of comparing the model data to the patient parameter data and the second IMD position data or performing the real-time computer simulations; and outputting to a user an indication of the position for the first IMD to be implanted within the patient based on the analysis.

Example 36

The computer-readable medium of example 35, wherein the patient parameter data includes at least one of a height of the patient, a weight of the patient, a chest circumference of the patient, a gender of the patient, or an age of the patient.

Example 37

The computer-readable medium of examples 35-36 or any combination thereof, wherein the instructions cause the at least one programmable processor to receive the second IMD position data by at least receiving an image or of the second IMD within the patient and determining the position of the second IMD within the patient based on the image of the patient.

Example 38

The computer-readable medium of examples 35-37 or any combination thereof, wherein the instructions cause the at least one programmable processor to output to the user the indication based on the analysis and further based on a strength of a signal received from the second IMD by an array of electrodes positioned on the patient.

Example 39

The computer-readable medium of examples 35-38 or any combination thereof, wherein outputting the indication includes outputting to the user the indication based on the analysis and further based on a strength of a signal received by the second IMD from an array of electrodes positioned on the patient.

Example 40

The computer-readable medium of examples 35-39 or any combination thereof, wherein the instructions cause the at least one programmable processor to receive the second IMD position data by at least receiving input data from a clinician, wherein the input data includes the position of the second IMD entered on a graphical representation of a human body.

Example 41

The computer-readable medium of examples 35-40 or any combination thereof, wherein the instructions cause the at least one programmable processor to output to the user the indication based on the analysis and further based on a strength of an electrocardiogram signal received by an array of electrodes positioned on the patient.

Example 42

A method is for identifying a position within a patient for a first implantable medical device (IMD) to be implanted to facilitate tissue conductive communication (TCC) between the first IMD and a second IMD implanted within the patient. The method includes storing model data that associates patient parameter data and second IMD position data with first IMD positions based on TCC communication performance. The method also includes receiving patient parameter data including a height of the patient, a weight of the patient, and a chest circumference of the patient and receiving an image of the second IMD within the patient. The method further includes determining a position of the second IMD within the patient and an orientation of the second IMD within the patient based on the image and performing analysis by at least one of comparing the model data to the patient parameter data and the second IMD position data, performing real-time computer simulations, or using a combination of comparing the model data to the patient parameter data and the second IMD position data or performing the real-time computer simulations. The method includes outputting to a user an indication of the position for the first IMD to be implanted within the patient based on the analysis.

Various aspects of this disclosure have been described. These and other aspects are within the scope of the following claims.

What is claimed is:

1. A method for identifying a position within a patient for a first implantable medical device (IMD) to be implanted to facilitate tissue conductive communication (TCC) between the first IMD and a second IMD implanted within the patient, the method comprising:
   storing model data that associates patient parameter data and second IMD position data with first IMD positions based on TCC communication performance;
   receiving patient parameter data indicating one or more anatomical or physiological parameters of the patient;
   receiving second IMD position data indicating a position of the second IMD within the patient and an orientation of the second IMD within the patient;
   performing analysis by at least one of:
      comparing the model data to the patient parameter data and the second IMD position data,
      performing real-time computer simulations, or
      using a combination of comparing the model data to the patient parameter data and the second IMD position data or performing the real-time computer simulations; and
   outputting to a user an indication of the position for the first IMD to be implanted within the patient based on the analysis.

2. The method of claim 1, wherein the patient parameter data includes at least one of a height of the patient or a weight of the patient.

3. The method of claim 1, wherein the patient parameter data includes a chest circumference of the patient.

4. The method of claim 1, wherein the patient parameter data includes at least one of a gender of the patient or an age of the patient.

5. The method of claim 1, wherein receiving the second IMD position data comprises:
   receiving an image of the second IMD within the patient; and
   determining the position of the second IMD within the patient based on the image of the patient.

6. The method of claim 1, wherein outputting the indication comprises outputting to the user the indication based on the analysis and further based on a strength of a signal received from the second IMD by an array of electrodes positioned on the patient.

7. The method of claim 1, wherein outputting the indication comprises outputting to the user the indication based on the analysis and further based on a strength of a signal received by the second IMD from an array of electrodes positioned on the patient.

8. The method of claim 1, further comprising determining the position for the first IMD to be implanted with the patient based on a type of the first IMD and a configuration of the first IMD, wherein outputting the indication is further based on determining the position for the first IMD.

9. The method of claim 1, wherein the model data includes a database associating IMD locations, patient parameter data, and TCC communication performance.

10. The method of claim 1, wherein receiving the second IMD position data comprises receiving input data from a clinician, wherein the input data includes the position of the second IMD entered on a graphical representation of a human body.

11. The method of claim 1, wherein outputting the indication comprises outputting to the user the indication based on the analysis and further based on a strength of an electrocardiogram signal received by an array of electrodes positioned on the patient.

12. The method of claim 1, wherein outputting the indication comprises:
   generating a graphical representation of at least part of a body;
   generating, based on the position for the first IMD, a graphical representation of a region for the first IMD; and
   causing a display device to display the graphical representation of the region for the first IMD in relation to the graphical representation of the at least part of the body.

13. A method for identifying a position within a patient for a first implantable medical device (IMD) to be implanted to facilitate tissue conductive communication (TCC) between the first IMD and a second IMD implanted within the patient, the method comprising:
   receiving an image of the second IMD within the patient;
   determining a position of the second IMD within the patient and an orientation of the second IMD within the patient based on the image;
   storing model data that associates patient parameter data and second IMD position data with first IMD positions based on TCC communication performance;
   receiving patient parameter data indicating one or more anatomical or physiological parameters of the patient;
   performing analysis by at least one of:
      comparing the model data to the patient parameter data and the second IMD position data,
      performing real-time computer simulations, or
      using a combination of comparing the model data to the patient parameter data and the second IMD position data or performing the real-time computer simulations; and
   outputting to a user an indication of the position for the first IMD to be implanted within the patient based on the analysis.

14. The method of claim 13, wherein the patient parameter data includes at least one of a height of the patient or a weight of the patient.

15. The method of claim 13, wherein the patient parameter data includes a chest circumference of the patient.

16. The method of claim 13, wherein the patient parameter data includes at least one of a gender of the patient or an age of the patient.

17. The method of claim 13, wherein outputting the indication comprises outputting to the user the indication based on the analysis and further based on a strength of a signal received from the second IMD by an array of electrodes positioned on the patient.

18. The method of claim 13, wherein outputting the indication comprises outputting to the user the indication based on the analysis and further based on a strength of a signal received by the second IMD from an array of electrodes positioned on the patient.

19. The method of claim 13, further comprising determining the position for the first IMD based on a type of the first IMD and a configuration of the first IMD, wherein outputting the indication is further based on determining the position for the first IMD.

20. The method of claim 13, wherein the model data includes a database associating IMD locations, patient parameter data, and TCC communication performance.

21. The method of claim 13, wherein outputting the indication comprises outputting to the user the indication based on the analysis and further based on a quantitative measurement of an electrocardiogram signal received by an array of electrodes positioned on the patient.

22. The method of claim 13, wherein outputting the indication comprises:
generating a graphical representation of at least part of a body;
generating, based on the position for the first IMD, a graphical representation of a region for the first IMD; and
causing a display device to display the graphical representation of the region for the first IMD in relation to the graphical representation of the at least part of the body.

23. A medical device system for identifying a position within a patient for a first implantable medical device (IMD) to be implanted to facilitate tissue conductive communication (TCC) between the first IMD and a second IMD implanted within the patient, the medical device system comprising:
a user interface; and
processing circuitry configured to:
store model data that associates patient parameter data and second IMD position data with first IMD positions based on TCC communication performance;
receive patient parameter data indicating one or more anatomical or physiological parameters of the patient;
receive second IMD position data indicating a position of the second IMD within the patient and an orientation of the second IMD within the patient; and
perform analysis by at least one of:
comparing the model data to the patient parameter data and the second IMD position data,
performing real-time computer simulations, or
using a combination of comparing the model data to the patient parameter data and the second IMD position data or performing the real-time computer simulations; and
output, via the user interface, an indication of the position for the first IMD to be implanted within the patient based on the analysis.

24. The medical device system of claim 23, wherein the processing circuitry is configured to receive the patient parameter data including at least one of a height of the patient or a weight of the patient.

25. The medical device system of claim 23, wherein the processing circuitry is configured to receive the patient parameter data including a chest circumference of the patient.

26. The medical device system of claim 23, wherein the processing circuitry is configured to receive the patient parameter data including at least one of a gender of the patient or an age of the patient.

27. The medical device system of claim 23, wherein the processing circuitry is configured to:
receive the second IMD position data including an image of the second IMD within the patient; and
determine the position of the second IMD within the patient based on the image of the patient.

28. The medical device system of claim 23, wherein the processing circuitry is configured to output to the user the indication based on the analysis and further based on a strength of a signal received from the second IMD by an array of electrodes positioned on the patient.

29. The medical device system of claim 23, wherein the processing circuitry is configured to output to the user the indication based on the analysis and further based on a strength of a signal received by the second IMD from an array of electrodes positioned on the patient.

30. The medical device system of claim 23, wherein the processing circuitry is configured to:
determine the position for the first IMD to be implanted with the patient based on a type of the first IMD and a configuration of the first IMD; and
output to the user the indication based on the analysis and further based on determining the position for the first IMD based on a type of the first IMD and a configuration of the first IMD.

31. The medical device system of claim 23, wherein the processing circuitry is configured to store model data including a database associating IMD locations, patient parameter data, and TCC communication performance.

32. The medical device system of claim 23, wherein the processing circuitry is configured to receive the second IMD position including input data from a clinician, wherein the input data includes the position of the second IMD entered on a graphical representation of a human body displayed on the user interface.

33. The medical device system of claim 23, wherein the processing circuitry is configured to output to the user the indication based on the analysis and further based on a strength of an electrocardiogram signal received by an array of electrodes positioned on the patient.

34. The medical device system of claim 23, wherein the processing circuitry is further configured to:
generate a graphical representation of at least part of a body; and
generate, based on the position for the first IMD, a graphical representation of a region for the first IMD,
wherein the processing circuitry is configured to output the indication comprises causing the user interface to display the graphical representation of the region for the first IMD in relation to the graphical representation of the at least part of the body.

35. A computer-readable medium comprising instructions for causing at least one programmable processor of a computing device to identify a position within a patient for a first implantable medical device (IMD) to be implanted to facilitate tissue conductive communication (TCC) between the first IMD and a second IMD implanted within the patient by at least:
   storing model data that associates patient parameter data and second IMD position data with first IMD positions based on TCC communication performance;
   receiving patient parameter data indicating one or more anatomical or physiological parameters of a patient;
   receiving second IMD position data indicating a position of a second IMD within the patient and an orientation of the second IMD within the patient;
   performing analysis by at least one of:
      comparing the model data to the patient parameter data and the second IMD position data,
      performing real-time computer simulations, or
      using a combination of comparing the model data to the patient parameter data and the second IMD position data or performing the real-time computer simulations; and
   outputting to a user an indication of the position for the first IMD to be implanted within the patient based on the analysis.

36. The computer-readable medium of claim 35, wherein the patient parameter data includes at least one of a height of the patient, a weight of the patient, a chest circumference of the patient, a gender of the patient, or an age of the patient.

37. The computer-readable medium of claim 35, wherein the instructions cause the at least one programmable processor to receive the second IMD position data by at least:
   receiving an image or of the second IMD within the patient; and
   determining the position of the second IMD within the patient based on the image of the patient.

38. The computer-readable medium of claim 35, wherein the instructions cause the at least one programmable processor to output to the user the indication based on the analysis and further based on a strength of a signal received from the second IMD by an array of electrodes positioned on the patient.

39. The computer-readable medium of claim 35, wherein outputting the indication comprises outputting to the user the indication based on the analysis and further based on a strength of a signal received by the second IMD from an array of electrodes positioned on the patient.

40. The computer-readable medium of claim 35, wherein the instructions cause the at least one programmable processor to receive the second IMD position data by at least receiving input data from a clinician, wherein the input data includes the position of the second IMD entered on a graphical representation of a human body.

41. The computer-readable medium of claim 35, wherein the instructions cause the at least one programmable processor to output to the user the indication based on the analysis and further based on a strength of an electrocardiogram signal received by an array of electrodes positioned on the patient.

42. A method for identifying a position within a patient for a first implantable medical device (IMD) to be implanted to facilitate tissue conductive communication (TCC) between the first IMD and a second IMD implanted within the patient, the method comprising:
   storing model data that associates patient parameter data and second IMD position data with first IMD positions based on TCC communication performance;
   receiving patient parameter data including a height of the patient, a weight of the patient, and a chest circumference of the patient;
   receiving an image of the second IMD within the patient;
   determining a position of the second IMD within the patient and an orientation of the second IMD within the patient based on the image;
   performing analysis by at least one of:
      comparing the model data to the patient parameter data and the second IMD position data,
      performing real-time computer simulations, or
      using a combination of comparing the model data to the patient parameter data and the second IMD position data or performing the real-time computer simulations; and
   outputting to a user an indication of the position for the first IMD to be implanted within the patient based on the analysis.

* * * * *